(12) United States Patent
Ohno et al.

(10) Patent No.: US 7,294,732 B2
(45) Date of Patent: Nov. 13, 2007

(54) SILICON COMPOUND

(75) Inventors: Kohji Ohno, Kyoto (JP); Yoshinobu Tsujii, Kyoto (JP); Takeshi Fukuda, Kyoto (JP)

(73) Assignee: Chisso Corporation, Osaka (JP)

( * ) Notice: Subject to any disclaimer, the term of this patent is extended or adjusted under 35 U.S.C. 154(b) by 395 days.

(21) Appl. No.: 10/523,702

(22) PCT Filed: Aug. 7, 2003

(86) PCT No.: PCT/JP03/10084

§ 371 (c)(1),
(2), (4) Date: Mar. 9, 2005

(87) PCT Pub. No.: WO2004/014924

PCT Pub. Date: Feb. 19, 2004

(65) Prior Publication Data

US 2005/0288468 A1    Dec. 29, 2005

(30) Foreign Application Priority Data

Aug. 7, 2002   (JP) .............. 2002-229790
Dec. 26, 2002  (JP) .............. 2002-378150

(51) Int. Cl.
*C07F 7/04* (2006.01)
*C08G 77/04* (2006.01)

(52) U.S. Cl. .................... 556/428; 528/34

(58) Field of Classification Search .............. None
See application file for complete search history.

(56) References Cited

U.S. PATENT DOCUMENTS 6,100,417 A   8/2000   Lichtenhan et al.

FOREIGN PATENT DOCUMENTS

JP   2001-247741   9/2001

*Primary Examiner*—Samuel Barts
(74) *Attorney, Agent, or Firm*—Wenderoth, Lind & Ponack, L.L.P.

(57) ABSTRACT

A silicon compound represented by Formula (1). In Formula (1), $R^1$ is a group independently selected respectively from the group consisting of a hydrogen atom, alkyl, substituted or non-substituted aryl and substituted or non-substituted arylalkyl, and $A^1$ is an organic group substituted with a halogenated sulfonyl group and is preferably a group represented by Formula (2). In Formula (2), X is halogen; $R^2$ is alkyl; a is an integer of 0 to 2; and $Z^1$ is a single bond or alkylene having a carbon number of 1 to 10.

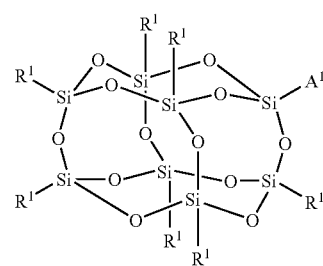

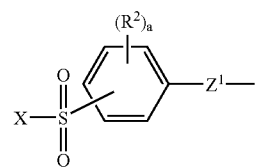

The silicon compound provided by the present invention is a silsesquioxane derivative having an excellent living polymerizable radical polymerization initiating function. For example, it is possible to commence polymerization by allowing an acryl base monomer to coexist to form an acryl base polymer making use of one point of the structure of the silsesquioxane in the present invention as a starting point. Because a halogenated sulfonyl group has a strong electrophilicity, it is possible to synthesize various silsesquioxane derivatives by reacting the silicon compound provided by the present invention with various nucleophilic reagents, and it can actively be used as an intermediate useful for organic synthesis.

24 Claims, No Drawings

SILICON COMPOUND

FIELD OF THE INVENTION

The present invention relates to a novel silicon compound characterized by having a polymerization initiating ability toward polymerizable monomers and a polymer obtained using the same.

BACKGROUND OF THE INVENTION

Macromolecular compounds have come to be used in various fields not only as a general purpose structure-forming material but also as a value added type material having high function and performance, and the importance of producing polymeric materials under precise design is increasing. Also in an organic-inorganic composite material containing silsesquioxane as an inorganic component, it is very important to create a novel functional polymeric material. Such material is obtained by synthesizing a macromolecular compound having a clear structure and precisely analyzing a molecular property thereof and a property as an aggregate respectively to thereby make correlation between both clear and setting it as a design guideline. However, conventional organic-inorganic composite materials do not necessarily contain a polymer which is controlled in a structure as an organic component, and a lot of them is obtained by mechanically blending silsesquioxane with organic polymers, so that it used to be very difficult to control the structure of composite materials as molecular assemblies.

DISCLOSURE OF THE INVENTION

An object of the present invention is to solve the problems described above regarding conventional organic-inorganic composite materials by providing a novel silicon compound characterized by having a living radical polymerization initiating ability toward polymerizable monomers and a polymer obtained using the same.

The problems described above can be solved by the present invention comprising the following structures.

[1] A silicon compound represented by Formula (1):

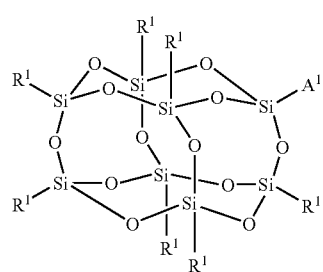

in Formula (1), seven $R^1$'s are groups independently selected respectively from the group consisting of hydrogen, alkyl, substituted or non-substituted aryl and substituted or non-substituted arylalkyl; $A^1$ is an organic group substituted with a halogenated sulfonyl group; in this alkyl, optional hydrogen may be substituted with fluorine, and optional —$CH_2$— may be substituted with —O—, —CH=CH—, cycloalkylene or cycloalkenylene; and in alkylene in this arylalkyl, optional hydrogen may be substituted with fluorine, and optional —$CH_2$— may be substituted with —O— or —CH=CH—.

[2] The silicon compound as described in the item [1], wherein seven $R^1$'s in Formula (1) are groups independently selected respectively from the group consisting of hydrogen, alkyl having a carbon number of 1 to 45, substituted or non-substituted aryl and substituted or non-substituted arylalkyl; in this alkyl having a carbon number of 1 to 45, optional hydrogen may be substituted with fluorine, and optional —$CH_2$— may be substituted with —O—, —CH=CH—, cycloalkylene or cycloalkenylene; and in alkylene in this arylalkyl, optional hydrogen may be substituted with fluorine, and optional —$CH_2$— may be substituted with —O— or —CH=CH—.

[3] The silicon compound as described in the item [1], wherein seven $R^1$'s in Formula (1) are groups independently selected respectively from the group consisting of hydrogen and alkyl having a carbon number of 1 to 30; and in the alkyl having a carbon number of 1 to 30, optional hydrogen may be substituted with fluorine, and optional —$CH_2$— may be substituted with —O— or cycloalkylene.

[4] The silicon compound as described in the item [1], wherein seven $R^1$'s in Formula (1) are groups independently selected respectively from the group consisting of alkenyl having a carbon number of 1 to 20 and a group in which optional —$CH_2$— is substituted with cycloalkenylene in alkyl having a carbon number of 1 to 20;

in the alkenyl having a carbon number of 1 to 20, optional hydrogen may be substituted with fluorine, and optional —$CH_2$— may be substituted with —O— or cycloalkylene; and in the group in which optional —$CH_2$— is substituted with cycloalkenylene in alkyl having a carbon number of 1 to 20, optional hydrogen may be substituted with fluorine.

[5] The silicon compound as described in the item [1], wherein seven $R^1$'s in Formula (1) are groups independently selected respectively from the group consisting of naphthyl and phenyl in which optional hydrogen may be substituted with halogen or alkyl having a carbon number of 1 to 10;

in the alkyl having a carbon number of 1 to 10, optional hydrogen may be substituted with fluorine, and optional —$CH_2$— may be substituted with —O—, —CH=CH—, cycloalkylene or phenylene.

[6] The silicon compound as described in the item [1], wherein seven $R^1$'s in Formula (1) are groups independently selected respectively from the group consisting of phenylalkyls in which optional hydrogen on a benzene ring may be substituted with halogen or alkyl having a carbon number of 1 to 12; in this alkyl having a carbon number of 1 to 12, optional hydrogen may be substituted with fluorine, and optional —$CH_2$— may be substituted with —O—, —CH=CH—, cycloalkylene or phenylene; and in alkylene in the phenylalkyl, which has a carbon number of 1 to 12, optional hydrogen may be substituted with fluorine, and optional —$CH_2$— may be substituted with —O— or —CH=CH—.

[7] The silicon compound as described in the item [1], wherein seven $R^1$'s in Formula (1) are groups independently selected respectively from the group consisting of alkyl having a carbon number of 1 to 8, phenyl, non-substituted naphthyl and phenylalkyl;

in the alkyl having 1 to 8 carbon atoms, optional hydrogen may be substituted with fluorine, and optional —CH$_2$— may be substituted with —O—, —CH═CH—, cycloalkylene or cycloalkenylene;

in the phenyl, optional hydrogen may be substituted with halogen, methyl or methoxy; in phenyl in the phenylalkyl, optional hydrogen may be substituted with fluorine, alkyl having a carbon number of 1 to 4, ethenyl or methoxy; and in alkylene in the phenylalkyl, it has a carbon number of 1 to 8, and optional —CH$_2$— may be substituted with —O— or —CH═CH—.

[8] The silicon compound as described in the item [1], wherein seven R$^1$'s in Formula (1) are one group selected from the group consisting of alkyl having a carbon number of 1 to 8, phenyl, non-substituted naphthyl and phenylalkyl;

in the alkyl having a carbon number of 1 to 8, optional hydrogen may be substituted with fluorine, and optional —CH$_2$— may be substituted with —O—, —CH═CH—, cycloalkylene or cycloalkenylene;

in the phenyl, optional hydrogen may be substituted with halogen, methyl or methoxy;

in phenyl in the phenylalkyl, optional hydrogen may be substituted with fluorine, alkyl having a carbon number of 1 to 4, ethenyl or methoxy; and in alkylene in the phenylalkyl, it has a carbon number of 1 to 8, and optional —CH$_2$— may be substituted with —O— or —CH═CH—.

[9] The silicon compound as described in the item [1], wherein seven R$^1$'s in Formula (1) are one group selected from the group consisting of phenyl, naphthyl and phenylalkyl; in the phenyl, optional hydrogen may be substituted with halogen, methyl or methoxy;

in phenyl in the phenylalkyl, optional hydrogen may be substituted with fluorine, alkyl having a carbon number of 1 to 4, ethenyl or methoxy; and in alkylene in the phenylalkyl, a carbon number thereof is 1 to 8, and optional —CH$_2$— may be substituted with —O—.

[10] The silicon compound as described in the item [1], wherein seven R$^1$'s in Formula (1) are ethyl, 2-methylpropyl, 2,4,4-trimethylpentyl, 3,3,3-trifluoropropyl, cyclopentyl, cyclohexyl or non-substituted phenyl.

[11] The silicon compound as described in the item [1], wherein seven R$^1$'s in Formula (1) are non-substituted phenyl.

[12] The silicon compound as described in any of the items [1] to [11], wherein A$^1$ in Formula (1) described in the item [1] is a group represented by Formula (2):

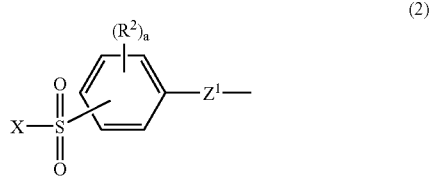

in Formula (2), X is halogen; R$^2$ is alkyl having a carbon number of 1 to 3; a is an integer of 0 to 2; Z$^1$ is a single bond or alkylene having a carbon number of 1 to 10; in this alkylene having a carbon number of 1 to 10, optional —CH$_2$— may be substituted with —O—, —COO— or —OCO—; and both of the bonding positions of halogenated sulfonyl and R$^2$ on a benzene ring are optional positions.

[13] The silicon compound as described in the item [12], wherein Z$^1$ in Formula (2) is Z$^2$—C$_2$H$_4$—; Z$^2$ is a single bond or alkylene having a carbon number of 1 to 8, and optional —CH$_2$— in this alkylene may be substituted with —O—, —COO— or —OCO—.

[14] The silicon compound as described in the item [12], wherein in Formula (2), Z$^1$ is —C$_2$H$_4$—; X is chlorine or bromine; and a is 0.

[15] A production process for the silicon compound represented by Formula (1) as described in the item [1], characterized by reacting a compound represented by Formula (3) with trichlorosilane having a halogenated sulfonyl group:

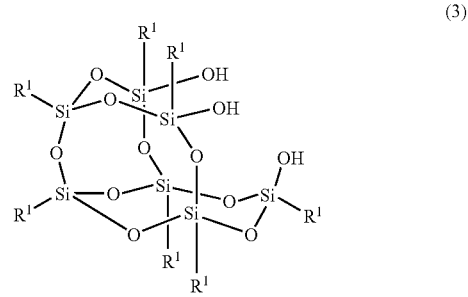

in Formula (3), seven R$^1$'s are groups independently selected respectively from the group consisting of hydrogen, alkyl, substituted or non-substituted aryl and substituted or non-substituted arylalkyl; in this alkyl, optional hydrogen may be substituted with fluorine, and optional —CH$_2$— may be substituted with —O—, —CH═CH—, cycloalkylene or cycloalkenylene; and in alkylene in the arylalkyl, optional hydrogen may be substituted with fluorine, and optional —CH$_2$— may be substituted with —O— or —CR═CR—.

[16] A production process for a silicon compound represented by Formula (5), characterized by reacting a compound represented by Formula (3) with a compound represented by Formula (4):

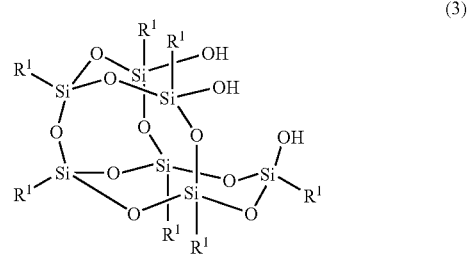

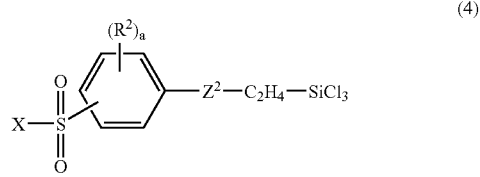

-continued (5)

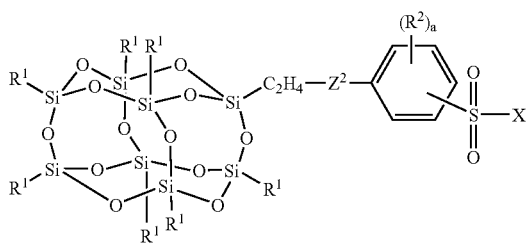

wherein R¹ in Formula (3) is one group selected from the group consisting of alkyl having a carbon number of 1 to 8, phenyl, non-substituted naphthyl and phenylalkyl; in the alkyl having a carbon number of 1 to 8, optional hydrogen may be substituted with fluorine, and optional —CH$_2$— may be substituted with —O—, —CH=CH—, cycloalkylene or cycloalkenylene; optional hydrogen in the phenyl may be substituted with halogen, methyl or methoxy; in the phenylalkyl, optional hydrogen on a benzene ring may be substituted with fluorine, alkyl having a carbon number of 1 to 4, ethenyl or methoxy, and optional —CH$_2$— in alkylene may be substituted with —O—; R¹ in Formula (5) has the same meaning as that of R¹ in Formula (3);

in Formula (4), X is halogen; R² is alkyl having a carbon number of 1 to 3; a is an integer of 0 to 2; Z² is a single bond or alkylene having 1 to 8 carbon atoms; in the alkylene having a carbon number of 1 to 8, optional —CH$_2$— may be substituted with —O—, —COO— or —OCO—; both of the bonding positions of halogenated sulfonyl and R² on a benzene ring are optional positions; and the meanings of X, R², and Z² in Formula (5) and the bonding positions of halogenated sulfonyl and R² on a benzene ring each are the same as those in Formula (4).

[17] A production process for the silicon compound represented by Formula (1) as described in the item [1], characterized by reacting a compound represented by Formula (6) with trichlorosilane having a halogenated sulfonyl group:

(6)

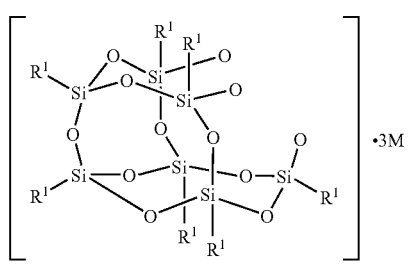

in Formula (6), seven R¹'s are groups independently selected respectively from the group consisting of hydrogen, alkyl, substituted or non-substituted aryl and substituted or non-substituted arylalkyl; M is a monovalent alkali metal atom; in this alkyl, optional hydrogen may be substituted with fluorine, and optional —CH$_2$— may be substituted with —O—, —CH=CH—, cycloalkylene or cycloalkenylene; and in alkylene in this arylalkyl, optional hydrogen may be substituted with fluorine, and optional —CH$_2$— may be substituted with —O— or —CH=CH—.

[18] A production process for a silicon compound represented by Formula (5), characterized by reacting a compound represented by Formula (6) with a compound represented by Formula (4):

(6)

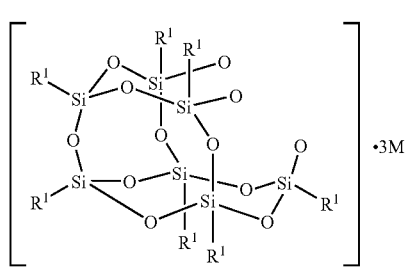

(4)

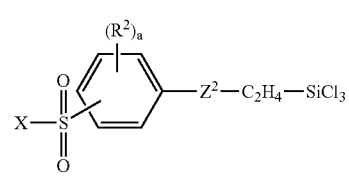

(5)

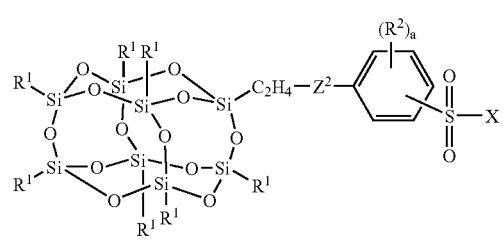

in Formula (6), R¹ is one group selected from the group consisting of alkyl having a carbon number of 1 to 8, phenyl, non-substituted naphthyl and phenylalkyl; M is a monovalent alkali metal atom; in the alkyl having a carbon number of 1 to 8, optional hydrogen may be substituted with fluorine, and optional —CH$_2$— may be substituted with —O—, —CH=CH—, cycloalkylene or cycloalkenylene; optional hydrogen in the phenyl may be substituted with halogen, methyl or methoxy; in the phenylalkyl, optional hydrogen on a benzene ring may be substituted with fluorine, alkyl having 1 to 4 carbon atoms, ethenyl or methoxy, and optional —CH$_2$— in alkylene may be substituted with —O—;

R¹ in Formula (5) has the same meaning as that of R¹ in Formula (6);

in Formula (4), X is halogen; R² is alkyl having 1 to 3 carbon atoms; a is an integer of 0 to 2; Z² is a single bond or alkylene having a carbon number of 1 to 8; in the alkylene having a carbon number of 1 to 8, optional —CH$_2$— may be substituted with —O—, —COO— or —OCO—; both of the bonding positions of halogenated sulfonyl and R² on a benzene ring are optional positions; and the meanings of X, R², a, and Z² in Formula (5) and the bonding positions of halogenated sulfonyl and R² on a benzene ring are the same as those in Formula (4).

[19] A polymer obtained by polymerizing a vinyl monomer using the silicon compound represented by Formula (1) as described in the item [1] as an initiator and a transition metal complex as a catalyst.

[20] A polymer represented by Formula (7) obtained by polymerizing a vinyl monomer using the silicon compound represented by Formula (1) as described in the item [18] as an initiator and a transition metal complex as a catalyst:

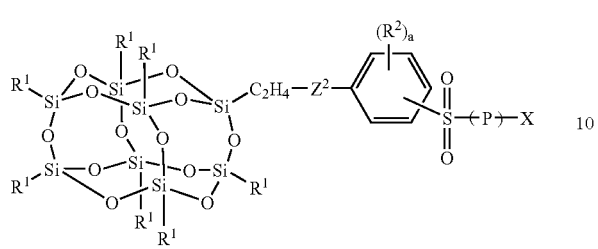

(7)

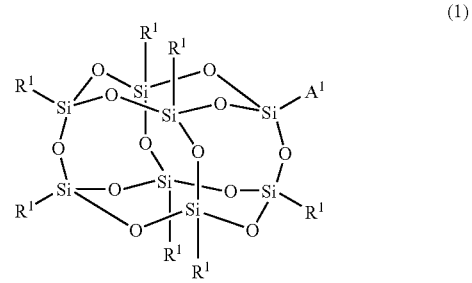

(1)

the meanings of $R^1$, $Z^2$, $R^2$, a, and X in Formula (7) and the bonding positions of halogenated sulfonyl and $R^2$ on a benzene ring are the same as those in Formula (6) as described in the item [18], and P is a vinyl polymer.

[21] The polymer as described in the item [19] or [20], wherein the vinyl monomer is at least one selected from the group consisting of a (meth)acrylic acid derivative and a styrene derivative.

[22] The polymer as described in the item [19] or [20], wherein the vinyl monomer is at least one selected from the group consisting of the (meth)acrylic acid derivatives.

[23] A polymerization process for a vinyl monomer characterized by using the silicon compound represented by Formula (1) as described in the item [1] as an initiator and using a transition metal complex as a catalyst.

[24] A production process for the polymer represented by Formula (7) as described in the item [20], characterized by polymerizing a vinyl monomer using the compound represented by Formula (5) as described in the item [18] as an initiator and using a transition metal complex as a catalyst.

BEST MODE FOR CARRYING OUT THE INVENTION

In the following explanations, the compound represented by Formula (1) shall be described as the compound (1). The compound represented by Formula (2) shall be described as the compound (2). The compounds represented by the other Formulas shall be described by the same abbreviation.

In the present invention, both of alkyl and alkylene may be linear groups or branched groups. For example, a group in which two —$CH_2$— in alkyl each are substituted with —O— and —CH=CH— is alkyloxyalkenyl or alkenyloxyalkyl, and any of alkyl, alkenylene, alkenyl and alkylene may be a linear group or a branched group. Both of cycloalkyl and cycloalkenyl may be groups having a cross-linked cyclic structure or may not be such groups. The term "optional" used in the present invention is used when it is shown that not only the position but also the number can optionally be selected. Provided that when it is defined that optional —$CH_2$— may be substituted with —O—, it does not include a case where plural continuous —$CH_2$— are substituted with —O—, and it does not include as well a case where —$CH_2$— bonded to a silicon atom is substituted with —O—.

In Formula (1), seven $R^1$'s are groups independently selected respectively from the group consisting of hydrogen, alkyl, substituted or non-substituted aryl and substituted or non-substituted arylalkyl. All $R^1$ is are preferably the same one group but may be constituted from two or more different groups. The examples of a case where seven $R^1$'s are constituted from different groups are a case where they are constituted from two or more alkyls, a case where they are constituted from two or more aryls, a case where they are constituted from two or more aralkyls, a case where they are constituted from hydrogen and at least one aryl, a case where they are constituted from at least one alkyl and at least one aryl, a case where they are constituted from at least one alkyl and at least one aralkyl and a case where they are constituted from at least one aryl and at least one aralkyl. They may be combinations other than these cases. The compound (1) having at least two different $R^1$ is can be obtained by using two or more raw materials when producing it. This raw material shall be described later.

When $R^1$ is alkyl, it has a carbon number of 1 to 45. The preferred carbon number is 1 to 30. The more preferred carbon number is 1 to 8. Optional hydrogen thereof may be substituted with fluorine, and optional —$CH_2$— may be substituted with —O—, —CH=CH—, cycloalkylene or cycloalkenylene. The preferred examples of the alkyl are non-substituted alkyl having a carbon number of 1 to 30, alkoxyalkyl having a carbon number of 2 to 29, a group in which one —$CH_2$— is substituted with cycloalkylene in alkyl having a carbon number of 1 to 8, alkenyl having a carbon number of 2 to 20, alkenyloxyalkyl having a carbon number of 2 to 20, alkyloxyalkenyl having a carbon number of 2 to 20, a group in which one —$CH_2$— is substituted with cycloalkenylene in alkyl having a carbon number of 1 to 8 and groups in which optional hydrogen(s) is/are substituted with fluorine in these groups. The preferred carbon numbers of cycloalkylene and cycloalkenylene are 3 to 8.

The examples of the non-substituted alkyl having a carbon number of 1 to 30 are methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethylpentyl, nonyl, decyl, undecyl, dodecyl, tetradecyl, hexadecyl, octadecyl, eicosyl, docosyl, triacontyl, and the like. The examples of the fluorinated alkyl having a carbon number of 1 to 30 are 3,3,3-trifluoropropyl, 3,3,4,4,5,5,6,6,6-nonadecafluorohexyl, tridecafluoro-1,1,2,2-tetrahydrooctyl, heptadecafluoro-1,1,2,2-tetrahydrodecyl, perfluoro-1H,1H,2H,2H-dodecyl, perfluoro-1H,1H,2H,2H-tetradecyl, and the like. The examples of the alkoxyalkyl having a carbon number of 2 to 29 are 3-methoxypropyl, methoxyethoxyundecyl, 3-heptafluoroisopropoxypropyl, and the like. The examples of the group in which one —$CH_2$— is substituted with cycloalkylene in alkyl having a carbon number of 1 to 8 are cyclohexylmethyl, adamantaneethyl, cyclopentyl, cyclohexyl, 2-bicycloheptyl, cyclooctyl, and the like. Cyclohexyl is an example in which —CH$_2$— in methyl is substituted with cyclohexylene. Cyclohexylmethyl is an example in which —CH$_2$— in ethyl is substituted with cyclohexylene.

The examples of the alkenyl having a carbon number of 2 to 20 are ethenyl, 2-propenyl, 3-butenyl, 5-hexenyl, 7-octenyl, 10-undecenyl, 21-docosenyl, and the like. The example of the alkenyloxyalkyl having a carbon number of 2 to 20 is allyloxyundecyl. The examples of the group in which one —CH$_2$— is substituted with cycloalkenylene in alkyl having a carbon number of 1 to 8 are 2-(3-cyclohexenyl)ethyl, 5-(bicycloheptenyl)ethyl, 2-cyclopentenyl, 3-cyclohexenyl, 5-norbornene-2-yl, 4-cyclooctenyl, and the like.

The examples of a case where R$^1$ in Formula (1) is substituted or non-substituted aryl are phenyl in which optional hydrogen may be substituted with halogen or alkyl having a carbon number of 1 to 10 and non-substituted naphthyl. The preferred examples of halogen are a fluorine atom, a chlorine atom and bromine. In the alkyl having a carbon number of 1 to 10, optional hydrogen may be substituted with fluorine, and optional —CH$_2$— may be substituted with —O—, —CH=CH— or phenylene. That is, the preferred examples of the case where R$^1$ is substituted or non-substituted aryl are non-substituted phenyl, non-substituted naphthyl, alkylphenyl, alkyloxyphenyl, alkenylphenyl, phenyl having as a substituent, a group in which optional —CH$_2$— in the alkyl having a carbon number of 1 to 10 is substituted with phenylene, groups in which optional hydrogen are substituted with halogen in these groups, and the like.

The examples of the halogenated phenyl are pentafluorophenyl, 4-chlorophenyl, 4-bromophenyl, and the like. The examples of the alkylphenyl are 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl, 2,4,6-tris(1-methylethyl)phenyl, and the like. The examples of the alkyloxyphenyl are (4-methoxy)phenyl, (4-ethoxy)phenyl, (4-propoxy)phenyl, (4-butoxy)phenyl, (4-pentyloxy)phenyl, (4-heptyloxy)phenyl, (4-decyloxy)phenyl, (4-octadecyloxy)phenyl, 4-(1-methylethoxy)phenyl, 4-(2-methylpropoxy)phenyl, 4-(1,1-dimethylethoxy)phenyl, and the like. The examples of the alkenylphenyl are 4-ethenylphenyl, 4-(1-methylethenyl)phenyl, 4-(3-butenyl)phenyl, and the like.

The examples of the phenyl having as a substituent, a group in which optional —CH$_2$— in the alkyl having a carbon number of 1 to 10 is substituted with phenylene are 4-(2-phenylethenyl)phenyl, 4-phenoxyphenyl, 3-(phenylmethyl)phenyl, biphenyl, terphenyl, and the like. 4-(2-Phenylethenyl)phenyl is an example in which one —CH$_2$— in ethyl of ethylphenyl is substituted with phenylene and in which the other —CH$_2$— is substituted with —CH=CH—.

The examples of the phenyl in which a part of hydrogens on a benzene ring is substituted with halogen and in which the other hydrogens are substituted with alkyl, alkyloxy or alkenyl are 3-chloro-4-methylphenyl, 2,5-dichloro-4-methylphenyl, 3,5-dichloro-4-methylphenyl, 2,3,5-trichloro-4-methylphenyl, 2,3,6-trichloro-4-methylphenyl, 3-bromo-4-methylphenyl, 2,5-dibromo-4-methylphenyl, 3,5-dibromo-4-methylphenyl, 2,3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, 2,3-difluoro-4-propoxyphenyl, 4-ethenyl-2,3,5,6-tetrafluorophenyl, and the like.

Next, the examples of a case where R$^1$ in Formula (1) is substituted or non-substituted arylalkyl shall be given. In alkylene of the arylalkyl, optional hydrogen may be substituted with fluorine, and optional —CH$_2$— may be substituted with —O— or —CH=CH—. The preferred example of the arylalkyl is phenylalkyl. In this case, the preferred carbon number of the alkylene is 1 to 12, and the more preferred carbon number is 1 to 8. The examples of the non-substituted phenylalkyl are phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl, 1-phenylhexyl, and the like.

In the phenylalkyl, optional hydrogen on a benzene ring may be substituted with halogen or alkyl having a carbon number of 1 to 12. In this alkyl having a carbon number of 1 to 12, optional hydrogen may be substituted with fluorine, and optional —CH$_2$— may be substituted with —O—, —CH=CH—, cycloalkylene or phenylene. The examples of the phenylalkyl in which optional hydrogen on phenyl are substituted with fluorine are 4-fluorophenylmethyl, 2,3,4,5,6-pentafluorophenylmethyl, 2-(2,3,4,5,6-pentafluorophenyl)ethyl, 3-(2,3,4,5,6-pentafluorophenyl)propyl, 2-(2-fluorophenyl)propyl, 2-(4-fluorophenyl)propyl, and the like.

The examples of the phenylalkyl in which hydrogens on a benzene ring are substituted with chlorine are 4-chlorophenylmethyl, 2-chlorophenylmethyl, 2,6-dichlorophenylmethyl, 2,4-dichlorophenylmethyl, 2,3,6-trichlorophenylmethyl, 2,4,6-trichlorophenylmethyl, 2,4,5-trichlorophenylmethyl, 2,3,4,6-tetrachlorophenylmethyl, 2,3,4,5,6-pentachlorophenylmethyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl, 4-(2,4,5-trichlorophenyl)butyl, 1-(3-chlorophenyl)ethyl, 1-(4-chlorophenyl)ethyl, 2-(4-chlorophenyl)propyl, 2-(2-chlorophenyl)propyl, 1-(4-chlorophenyl)butyl, and the like.

The examples of the phenylalkyl in which hydrogens on phenyl are substituted with bromine are 2-bromophenylmethyl, 4-bromophenylmethyl, 2,4-dibromophenylmethyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl, 2-(4-bromophenyl)propyl, and the like.

The examples of the phenylalkyl in which hydrogens on a benzene ring are substituted with alkyl having a carbon number of 1 to 12 are 2-methylphenylmethyl, 3-methylphenylmethyl, 4-methylphenylmethyl, 4-dodecylphenylmethyl, 3,5-dimethylphenylmethyl, 2-(4-methylphenyl)ethyl, 2-(3-methylphenyl)ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethylphenyl)-propyl, 2-(2,4-dimethylphenyl)propyl, 2-(3,4-dimethylphenyl)propyl, 2-(2,5-dimethylphenyl)butyl, (4-(1-methylethyl)phenyl)methyl, 2-(4-(1,1-dimethylethyl)phenyl)ethyl, 2-(4-(1-methylethyl)phenyl)propyl, 2-(3-(1-methylethyl)phenyl)propyl, and the like.

The examples of the phenylalkyl in which hydrogens on a benzene ring are substituted with alkyl having a carbon number of 1 to 12 and in which hydrogens in this alkyl are substituted with fluorine are 3-(trifluoromethyl)phenylethyl, 2-(4-trifluoromethylphenyl)ethyl, 2-(4-nonafluorobutylphenyl)ethyl, 2-(4-tridecafluorohexylphenyl)ethyl, 2-(4-heptadecafluorooctylphenyl)ethyl, 1-(3-trifluoromethylphenyl)ethyl, 1-(4-trifluoromethylphenyl)ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl)propyl, 1-methyl-1-(4-nonafluorobutylphenyl)ethyl, 2-(4-tridecafluorohexylphenyl)propyl, 1-methyl-1-(4-tridecafluorohexylphenyl)ethyl, 2-(4-heptadecafluorooctylphenyl)propyl, 1-methyl-1-(4-heptadecafluorooctyl)phenyl)ethyl, and the like.

The examples of the phenylalkyl in which hydrogens on a benzene ring are substituted with alkyl having a carbon number of 1 to 12 and in which —CH$_2$—in this alkyl is substituted with —CH═CH— are 2-(4-ethenylphenyl)ethyl, 1-(4-ethenylphenyl)ethyl, 1-(2-(2-propenyl)phenyl)ethyl, and the like. The examples of the phenylalkyl in which hydrogens on a benzene ring are substituted with alkyl having a carbon number of 1 to 12 and in which —CH$_2$— in this alkyl is substituted with —O— are 4-methoxyphenylmethyl, 3-methoxyphenylmethyl, 4-ethoxyphenylmethyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, 2-(3-methoxymethyl)phenyl)ethyl, 3-(2-nonadecafluorodecenyloxyphenyl)propyl, and the like.

The examples of the phenylalkyl in which hydrogens on a benzene ring are substituted with alkyl having a carbon number of 1 to 12 and in which one of —CH$_2$— in this alkyl is substituted with cycloalkylene are, to give examples thereof including a case where another —CH$_2$— is substituted with —O—, are cyclopentylphenylmethyl, cyclopentyloxyphenylmethyl, cyclohexylphenylmethyl, cyclohexylphenylethyl, cyclohexylphenylpropyl, cyclohexyloxyphenylmethyl, and the like. The examples of the phenylalkyl in which hydrogens on a benzene ring are substituted with alkyl having a carbon number of 1 to 12 and in which one of —CH$_2$— in this alkyl is substituted with phenylene are, to give examples thereof including a case where another —CH$_2$— is substituted with —O—, are 2-(4-phenoxyphenyl)ethyl, 2-(4-phenoxyphenyl)propyl, 2-(2-phenoxyphenyl)propyl, 4-biphenylylmethyl, 3-biphenylylethyl, 4-biphenylylethyl, 4-biphenylylpropyl, 2-(2-biphenylyl)propyl, 2-(4-biphenylyl)propyl, and the like.

The examples of the phenylalkyl in which at least two hydrogens on a benzene ring are substituted with different groups are 3-(2,5-dimethoxy-3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmethyl, 2,3-dichloro-4-methylphenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenylmethyl, (2,3,4,6-tetrachloro-5-methylphenyl)methyl, 2,3,4,5-tetrachloro-6-methylphenylmethyl, 4-chloro-3,5-dimethylphenylmethyl, 2-chloro-3,5-dimethylphenylmethyl, 2,4-dichloro-3,5-dimethylphenylmethyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenylmethyl, 6-bromo-2-methylphenylmethyl, 3-bromo-4-methylphenylmethyl, 2,3-dibromo-(4-methylphenylmethyl, 2,3,5-tribromo-4-methylphenylmethyl, 2,3,5,6-tetrabromo-4-methylphenylmethyl, 11-(3-chloro-4-methoxyphenyl)undecyl, and the like.

The most preferred examples of phenyl in the phenylalkyl are non-substituted phenyl and phenyl having at least one of fluorine, alkyl having a carbon number of 1 to 4, ethenyl and methoxy as a substituent.

The examples of the phenylalkyl in which —CH$_2$— in alkylene is substituted with —O— or —CH═CH— are 2-phenoxyethyl, 3-phenoxypropyl, 4-phenoxybutyl, 1-phenylethenyl, 2-phenylethenyl, 3-phenyl-2-propenyl, 4-phenyl-4-pentenyl, 13-phenyl-12-tridecenyl, and the like. The examples of the phenylalkyl in which hydrogen on a benzene ring is substituted with fluorine or methyl are 4-fluorophenylethenyl, 2,3-difluorophenylethenyl, 2,3,4,5,6-pentafluorophenylethenyl, 4-methylphenylethenyl, and the like.

The most preferred examples of R$^1$ are alkyl having a carbon number of 1 to 8 (for example, ethyl, isobutyl and isooctyl), phenyl, halogenated phenyl, phenyl having at least one methyl, methoxyphenyl, naphthyl, phenylmethyl, phenylethyl, phenylbutyl, 2-phenylpropyl, 1-methyl-2-phenylethyl, pentafluoropropyl, 4-ethylphenylethyl, 3-ethylphenylethyl, 4-(1,1-dimethylethyl)phenylethyl, 4-ethenylphenylethyl, 1-(4-ethenylphenyl)ethyl, 4-methoxyphenylpropyl, phenoxyethyl and phenoxypropyl.

A$^1$ in Formula (1) is an organic group having a halogenated sulfonyl group. An atom transfer radical polymerization method is known as a polymerization method using this halogenated sulfonyl group as an initiating group for radical polymerization. In this method, a metal complex comprising the eighth, ninth, tenth or eleventh element in the periodic table as a central metal atom is used as a catalyst. It is known that the halogenated sulfonyl group has an excellent polymerization initiating ability in this atom transfer radical polymerization. In addition thereto, it is well known as well that this polymerization is living polymerization-like. That is, the compound (1) has an excellent polymerization initiating ability under the presence of a transition metal complex and can continue to maintain a living polymerizability. The compound (1) can start polymerization of all radically polymerizable monomers.

A halogenated sulfonyl group has a strong electrophilicity, and therefore various silsesquioxane derivatives can be synthesized by reacting the silicon compound of the present invention with various nucleophilic reagents. For example, possible are conversion into sulfonic acid by hydrolysis under an acid condition, conversion into sulfonic acid by hydrolysis under an acid condition and then conversion into sulfonic acid salt by treating with sodium hydroxide, conversion into sulfonic acid esters by reacting with various alcohols under a basic condition and conversion into sulfonamide by treating with ammonia or amine. It is possible to make use of the silicon compound of the present invention as a protective group because it has such reactivity, and it is possible as well to make use of a derivative of sulfonamide as a sulfa agent (for example, antibacterial agent). It is possible as well to carry out conversion into a mercapto group by using various reducing agents (for example, aluminum lithium hydride). It can be derived into aromatic sulfone by various aromatic Grignard reagents. That is, the compound (1) can be used not only as a polymerization initiator but also as an intermediate useful for various organic syntheses.

The preferred exampled of A$^1$ is a group represented by Formula (2):

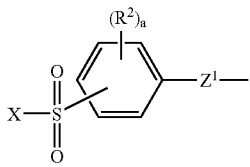

(2)

in Formula (2), X is halogen; $R^2$ is alkyl having 1 to 3 carbon atoms; a is an integer of 0 to 2; and $Z^1$ is a single bond or alkylene having a carbon number of 1 to 10. In the alkylene having 1 to 10 carbon atoms, optional —$CH_2$— may be substituted with —O—, —COO— or —OCO—. Both of the bonding positions of halogenated sulfonyl and $R^2$ on a benzene ring are optional positions. $Z^1$ is preferably $Z^2$—$C_2H_4$—. In this case, $Z^2$ is a single bond or alkylene having a carbon number of 1 to 8, and at least one —$CH_2$— which is not adjacent in this alkylene may be substituted with —O—, —COO— or —OCO—. The most preferred example of $Z^2$ is —$C_2H_4$—. The examples of halogen are Cl, Br and I. An Initiating Group for the Atom Transfer Radical polymerization is most preferably Cl and Br. Preferred a is 0.

Next, a part of the specific examples of the silicon compound of the present invention shall be shown in Tables 2 and 3 using codes defined in Table 1. These examples are examples of the following Formula (8). In this formula, $R^1$ is ethyl, 2-methylpropyl, 2,4,4-trimethylpentyl, cyclopentyl or phenyl, and $Z^2$ is a single bond or —$CH_2$—.

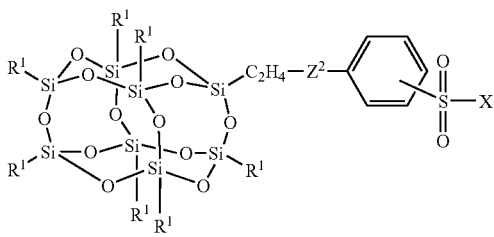

(8)

TABLE 1

| Code | Chemical formula |
|---|---|
| Et | —$C_2H_5$ |
| iBu | —$CH_2CH(CH_3)_2$ |
| iOc | —$CH_2CH(CH_3)CH_2C(CH_3)_3$ |
| TFPr | —$CH_2CH_2CF_3$ |
| CP | cyclopentyl |
| CH | cyclohexyl |
| Ph | phenyl |
| — | Single bond |
| C1 | —$CH_2$— |
| C2 | —$C_2H_4$— |
| C3 | —$C_3H_6$— |
| C4 | —$C_4H_8$— |
| C5 | —$C_5H_{10}$— |

TABLE 1-continued

| Code | Chemical formula |
|---|---|
| CL | —Cl |
| BR | —Br |

TABLE 2

| No. | $R^1$ | $Z^2$ | X | Formula (8) |
|---|---|---|---|---|
| 1 | Et | — | CL | (Et—)$_7$(CL—$SO_2$—Ph—C2—)$Si_8O_{12}$ |
| 2 | iBu | — | CL | (iBu—)$_7$(CL—$SO_2$—Ph—C2—)$Si_8O_{12}$ |
| 3 | iOc | — | CL | (iOc—)$_7$(CL—$SO_2$—Ph—C2—)$Si_8O_{12}$ |
| 4 | TFPr | — | CL | (TFPr—)$_7$(CL—$SO_2$—Ph—C2—)$Si_8O_{12}$ |
| 5 | CP | — | CL | (CP—)$_7$(CL—$SO_2$—Ph—C2—)$Si_8O_{12}$ |
| 6 | CH | — | CL | (CH—)$_7$(CL—$SO_2$—Ph—C2—)$Si_8O_{12}$ |
| 7 | Ph | — | CL | (Ph—)$_7$(CL—$SO_2$—Ph—C2—)$Si_8O_{12}$ |
| 8 | Et | C1 | CL | (Et—)$_7$(CL—$SO_2$—Ph—C3—)$Si_8O_{12}$ |
| 9 | iBu | C1 | CL | (iBu—)$_7$(CL—$SO_2$—Ph—C3—)$Si_8O_{12}$ |
| 10 | iOc | C1 | CL | (iOc—)$_7$(CL—$SO_2$—Ph—C3—)$Si_8O_{12}$ |
| 11 | TFPr | C1 | CL | (TFPr—)$_7$(CL—$SO_2$—Ph—C3—)$Si_8O_{12}$ |
| 12 | CP | C1 | CL | (CP—)$_7$(CL—$SO_2$—Ph—C3—)$Si_8O_{12}$ |
| 13 | CH | C1 | CL | (CH—)$_7$(CL—$SO_2$—Ph—C3—)$Si_8O_{12}$ |
| 14 | Ph | C1 | CL | (Ph—)$_7$(CL—$SO_2$—Ph—C3—)$Si_8O_{12}$ |
| 15 | Et | C2 | CL | (Et—)$_7$(CL—$SO_2$—Ph—C4—)$Si_8O_{12}$ |
| 16 | iBu | C2 | CL | (iBu—)$_7$(CL—$SO_2$—Ph—C4—)$Si_8O_{12}$ |
| 17 | iOc | C2 | CL | (iOc—)$_7$(CL—$SO_2$—Ph—C4—)$Si_8O_{12}$ |
| 18 | TFPr | C2 | CL | (TFPr—)$_7$(CL—$SO_2$—Ph—C4—)$Si_8O_{12}$ |
| 19 | CP | C2 | CL | (CP—)$_7$(CL—$SO_2$—Ph—C4—)$Si_8O_{12}$ |
| 20 | CH | C2 | CL | (CH—)$_7$(CL—$SO_2$—Ph—C4—)$Si_8O_{12}$ |
| 21 | Ph | C2 | CL | (Ph—)$_7$(CL—$SO_2$—Ph—C4—)$Si_8O_{12}$ |
| 22 | Et | C3 | CL | (Et—)$_7$(CL—$SO_2$—Ph—C5—)$Si_8O_{12}$ |
| 23 | iBu | C3 | CL | (iBu—)$_7$(CL—$SO_2$—Ph—C5—)$Si_8O_{12}$ |
| 24 | iOc | C3 | CL | (iOc—)$_7$(CL—$SO_2$—Ph—C5—)$Si_8O_{12}$ |
| 25 | TFPr | C3 | CL | (TFPr—)$_7$(CL—$SO_2$—Ph—C5—)$Si_8O_{12}$ |
| 26 | CP | C3 | CL | (CP—)$_7$(CL—$SO_2$—Ph—C5—)$Si_8O_{12}$ |
| 27 | CH | C3 | CL | (CH—)$_7$(CL—$SO_2$—Ph—C5—)$Si_8O_{12}$ |
| 28 | Ph | C3 | CL | (Ph—)$_7$(CL—$SO_2$—Ph—C5—)$Si_8O_{12}$ |

TABLE 3

| No. | $R^1$ | $Z^2$ | X | Formula (8) |
|---|---|---|---|---|
| 1 | Et | — | BR | (Et—)$_7$(BR—$SO_2$—Ph—C2—)$Si_8O_{12}$ |
| 2 | iBu | — | BR | (iBu—)$_7$(BR—$SO_2$—Ph—C2—)$Si_8O_{12}$ |
| 3 | iOc | — | BR | (iOc—)$_7$(BR—$SO_2$—Ph—C2—)$Si_8O_{12}$ |
| 4 | TFPr | — | BR | (TFPr—)$_7$(BR—$SO_2$—Ph—C2—)$Si_8O_{12}$ |
| 5 | CP | — | BR | (CP—)$_7$(BR—$SO_2$—Ph—C2—)$Si_8O_{12}$ |
| 6 | CH | — | BR | (CH—)$_7$(BR—$SO_2$—Ph—C2—)$Si_8O_{12}$ |
| 7 | Ph | — | BR | (Ph—)$_7$(BR—$SO_2$—Ph—C2—)$Si_8O_{12}$ |
| 8 | Et | C1 | BR | (Et—)$_7$(BR—$SO_2$—Ph—C3—)$Si_8O_{12}$ |
| 9 | iBu | C1 | BR | (iBu—)$_7$(BR—$SO_2$—Ph—C3—)$Si_8O_{12}$ |
| 10 | iOc | C1 | BR | (iOc—)$_7$(BR—$SO_2$—Ph—C3—)$Si_8O_{12}$ |
| 11 | TFPr | C1 | BR | (TFPr—)$_7$(BR—$SO_2$—Ph—C3—)$Si_8O_{12}$ |
| 12 | CP | C1 | BR | (CP—)$_7$(BR—$SO_2$—Ph—C3—)$Si_8O_{12}$ |
| 13 | CH | C1 | BR | (CH—)$_7$(BR—$SO_2$—Ph—C3—)$Si_8O_{12}$ |
| 14 | Ph | C1 | BR | (Ph—)$_7$(BR—$SO_2$—Ph—C3—)$Si_8O_{12}$ |
| 15 | Et | C2 | BR | (Et—)$_7$(BR—$SO_2$—Ph—C4—)$Si_8O_{12}$ |
| 16 | iBu | C2 | BR | (iBu—)$_7$(BR—$SO_2$—Ph—C4—)$Si_8O_{12}$ |
| 17 | iOc | C2 | BR | (iOc—)$_7$(BR—$SO_2$—Ph—C4—)$Si_8O_{12}$ |
| 18 | TFPr | C2 | BR | (TFPr—)$_7$(BR—$SO_2$—Ph—C4—)$Si_8O_{12}$ |
| 19 | CP | C2 | BR | (CP—)$_7$(BR—$SO_2$—Ph—C4—)$Si_8O_{12}$ |
| 20 | CH | C2 | BR | (CH—)$_7$(BR—$SO_2$—Ph—C4—)$Si_8O_{12}$ |
| 21 | Ph | C2 | BR | (Ph—)$_7$(BR—$SO_2$—Ph—C4—)$Si_8O_{12}$ |
| 22 | Et | C3 | BR | (Et—)$_7$(BR—$SO_2$—Ph—C5—)$Si_8O_{12}$ |
| 23 | iBu | C3 | BR | (iBu—)$_7$(BR—$SO_2$—Ph—C5—)$Si_8O_{12}$ |
| 24 | iOc | C3 | BR | (iOc—)$_7$(BR—$SO_2$—Ph—C5—)$Si_8O_{12}$ |
| 25 | TFPr | C3 | BR | (TFPr—)$_7$(BR—$SO_2$—Ph—C5—)$Si_8O_{12}$ |
| 26 | CP | C3 | BR | (CP—)$_7$(BR—$SO_2$—Ph—C5—)$Si_8O_{12}$ |
| 27 | CH | C3 | BR | (CH—)$_7$(BR—$SO_2$—Ph—C5—)$Si_8O_{12}$ |
| 28 | Ph | C3 | BR | (Ph—)$_7$(BR—$SO_2$—Ph—C5—)$Si_8O_{12}$ |

The examples shown in Table 2 and Table 3 are the preferred examples of the silicon compound of the present invention. The compound in which $R^1$ in Formula (1) is non-substituted phenyl is most preferred.

Next, the production process for the silicon compound of the present invention shall be explained. The referred raw material of the present invention is a silicon compound having a silanol group represented by Formula (3):

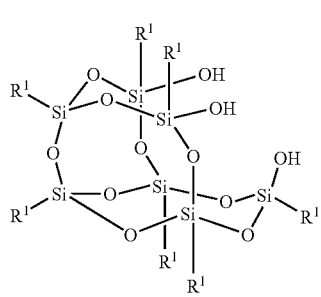

(3)

$R^1$ in Formula (3) is the same as $R^1$ in Formula (1). Such compound can be synthesized by hydrolyzing chlorosilane and further ripening it. For example, Frank J. Feher et al. obtain a compound in which $R^1$ is cyclopentyl in Formula (3) by reacting cyclopentyltrichlorosilane in a water-acetone mixed solvent under a room temperature or refluxing temperature and further ripening it for 2 weeks (Organometallics, 10, 2526-(1991), Chemical European Journal, 3, No. 6, 900-(1997)).

The compound (1) can be produced by reacting the compound (3) with trichlorosilane having a halogenated sulfonyl group making use of the reactivity of silanol (Si—OH).

Preferred trichlorosilane having a halogenated sulfonyl group is a compound (4). A compound (5) is obtained by reacting the compound (3) with the compound (4):

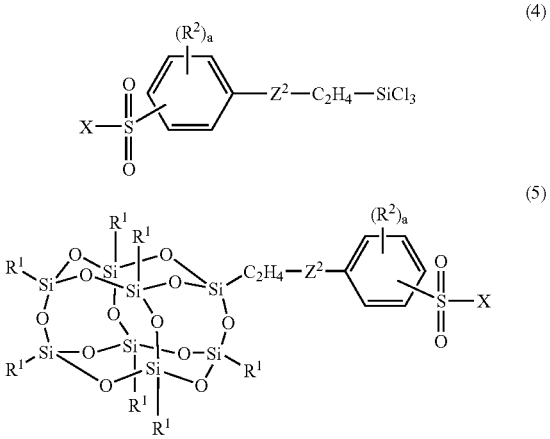

Considering to obtain the compound (3) as a commercially available product, the preferred example of $R^1$ in Formula (3) is one group selected from the group consisting of alkyl having a carbon number of 1 to 8, phenyl, non-substituted naphthyl and phenylalkyl. Provided that in the alkyl having a carbon number of 1 to 8, optional hydrogen may be substituted with fluorine, and optional —$CH_2$— may be substituted with —O—, —CH=CH—, cycloalkylene or cycloalkenylene. Optional hydrogen in the phenyl may be substituted with halogen, methyl or methoxy. In the phenylalkyl, optional hydrogen on a benzene ring may be substituted with fluorine, alkyl having a carbon number of 1 to 4, ethenyl or methoxy, and optional —$CH_2$— in alkylene may be substituted with —O—. The other codes in Formula (4) and Formula (5) have the same meanings as described above. The bonding positions of the halogenated sulfonyl group and $R^2$ are the same as described above.

In order to synthesize the compound (5) from the compound (3) and the compound (4), capable of being adopted is a method called "Corner-capping reaction" (it is reaction making use of so-called nucleophilic substitution and described in, for example, Macromolecules, 28, 8435-(1995)). The examples of the compound (4) are 2-(4-chlorosulfonyl)ethyltrichlorosilane and 3-(4-chlorosulfonyl)propyltrichlorosilane, but they shall not be restricted to them.

The selecting conditions of a solvent used for this nucleophilic substitution reaction is that it is not reacted with the compound (3) and the compound (4) and that it is sufficiently dehydrated. The examples of the solvent are tetrahydrofuran, toluene, dimethylformamide, and the like. The most preferred solvent is tetrahydrofuran which is well dehydrated. The preferred use amount of the compound (4) is 1 to 5 times in terms of an equivalent ratio based on an Si—OH group in the case where it is reacted with the whole Si—OH (silanol) group of the compound (3). In this reaction, hydrogen chloride is generated by reacting hydrogen of silanol with chlorine of chlorosilane, and therefore this hydrogen chloride has to be removed from the reaction system. A method for removing hydrogen chloride shall not be restricted, and triethylamine is most preferably used. The preferred use amount of triethylamine is 3 to 5 times in terms of an equivalent ratio based on an Si—OH group of the compound (3). The reaction temperature is a temperature which does not bring about side reactions at the same time and which can allow quantitative nucleophilic substitution reaction to proceed. However, in charging the raw materials, it is most preferably carried out under a low temperature condition, for example, in an ice bath, and then it may be carried out under a a room temperature. The reaction time shall not specifically be restricted as long as it is sufficient time for allowing quantitative nucleophilic substitution reaction to proceed, and the intended silicon compound can be obtained usually in 13 hours.

Another preferred raw material used in the present invention is a silsesquioxane compound represented by Formula (6):

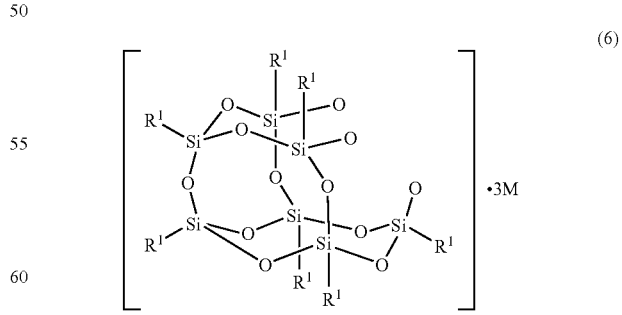

(6)

The compound (6) is obtained by reacting a silsesquioxane oligomer obtained by hydrolyzing a silane compound having a trifunctional hydrolyzable group with monovalent alkali metal hydroxide in an organic solvent. It is obtained as well by hydrolyzing and condensing a silane compound having a trifunctional hydrolyzable group under the presence of an organic solvent, water and alkali metal hydroxide. In the case of any methods, the compound (6) can be produced at a high yield for short time (for example, refer to the specification of Application No. PCT/JP02/04776). The compound (6) shows a higher reactivity than that of a silanol group in the compound (3). Accordingly, if this compound is used as the raw material, the derivative thereof can readily be synthesized at a high yield. Further, it has —ONa as a reactive group, and therefore if chlorosilanes are used for the synthetic reaction of the derivative, hydrogen chloride is not produced. Accordingly, the reaction operation can be facilitated, and it is possible to completely react it. That is, the compound (1) can readily be obtained from the compound (6) and trichlorosilane having a halogenated sulfonyl group.

Also when using the compound (6), it is preferably reacted with the compound (4) described above to prepare the compound (5). $R^1$ in Formula (6) is the same as $R^1$ in Formula (1), and the preferred examples thereof are the same as those in Formula (3). M in Formula (6) is a monovalent alkali metal atom. The preferred alkali metal is sodium and potassium. The most preferred example is sodium. Reaction in which the compound (6) is reacted with the compound (4) to prepare the compound (5) can be carried out as well in the same manner as in a case where the compound (3) is used. The preferred use amount of the compound (4) is 1 to 5 times in terms of an equivalent ratio based on an Si—ONa group of the compound (6). In this reaction, triethylamine does not have to be used for the purpose of removing hydrogen chloride. However, triethylamine may be used as a catalytic role for allowing the reaction to quickly go on. When using triethylamine, it is added in an amount of 3 to 5 times in terms of an equivalent ratio based on an Si—ONa group in the compound (6). A solvent, reaction temperature and reaction time used in the reaction are the same as in the reaction in which the compound (3) is used.

If a distillation method is applied in order to remove the unreacted raw material compounds and solvent (hereinafter referred to as "impurities" in combination), the intended compound is likely to be decomposed by maintaining for long time under a high temperature condition. Accordingly, a refining method by recrystallization operation is preferably used in order to efficiently remove the impurities without damaging a purity of the compound (5). This refining method is carried out in the following manner. First, the compound (5) is dissolved in a solvent which dissolves both of the compound (5) and the impurities. In this case, the preferred concentration is, roughly speaking, 1 to 15% by weight. Next, the above solution is concentrated under a reduced pressure condition by means of a concentrating device, for example, a rotary evaporator until crystal is started depositing. Then, the pressure is returned to an atmospheric pressure, and the reaction liquid is maintained at a room temperature or under a low temperature condition. Thereafter, the reaction liquid is subjected to filter filtration or centrifugal separation, whereby a solid matted component deposited can be separated from the solvent containing impurities. It is a matter of course that the intended compound is contained as well in the solvent containing the impurities, so that a recovering rate of the compound (5) can be raised by repeatedly carrying out the operation described above.

The selection conditions of the preferred solvent used for recrystallization are no reaction with the compound (6), dissolving the compound (6) and impurities at a stage before concentration, dissolving only the impurities and efficiently depositing the compound (6) in concentration and having a relatively low boiling point. The examples of the preferred solvent satisfying such conditions are esters. The particularly preferred solvent is ethyl acetate. The frequency of repeating the recrystallization operation is advisably increased in order to further raise the refining degree.

Next, an addition-polymerizable monomer for which the compound (1) can be used as a polymerization initiator shall be explained. This addition-polymerizable monomer is a monomer having at least one addition-polymerizable double bond. One of the examples of a monofunctional monomer having one addition-polymerizable double bond is a (meth) acrylic acid derivative. The specific examples thereof are (meth)acrylic acid, methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, n-hexyl (meth) acrylate, cyclohexyl (meth)acrylate, n-heptyl (meth)acrylate, n-octyl (meth)acrylate, 2-ethylhexyl (meth)acrylate, nonyl (meth)acrylate, decyl (meth)acrylate, dodecyl (meth) acrylate, phenyl (meth)acrylate, toluyl (meth)acrylate, benzyl (meth)acrylate, 2-methoxyethyl (meth)acrylate, 3-methoxypropyl (meth)acrylate, 3-methoxybutyl (meth)acrylate, 2-hydroxyethyl (meth)acrylate, 2-hydroxypropyl (meth) acrylate, stearyl (meth)acrylate, glycidyl (meth)acrylate, 3-ethyl-3-(meth)acryloyloxymethyloxetane, 4-(meth)acryloyloxymethyl-2,2-dimethyl-1,3-dioxolane, 4-(meth)acryloyloxymethyl-2-methyl-2-ethyl-1,3-dioxolane, 4-(meth) acryloyloxymethyl-2-methyl-2-isobutyl-1,3-dioxolane, 4-(meth)acryloyloxymethyl-2-cyclohexyl-1,3-dioxolane, 2-(meth)acryloyloxyethyl-isocyanate, 2-aminoethyl (meth) acrylate, 2-(2-bromopropanoylyloxy)ethyl (meth)acrylate, 2-(2-bromoisobutyryloxy)ethyl (meth)acrylate, 1-(meth) acryloxy-2-phenyl-2-(2,2,6,6-tetramethylpiperidinyloxy) ethane, (1-(4-((4-(meth)acryloxy)ethoxyethyl)phenylethoxy)piperidine, γ-(methacryloyloxypropyl) trimethoxysilane, 3-(3,5,7,9,11,13,15-heptaethylpentacyclo-[9.5.1.1$^{3,9}$.1$^{5,15}$.1$^{7,13}$] octasiloxane-1-yl)propyl (meth) acrylate, 3-(3,5,7,9,11,13,15-heptaisobutyl-pentacyclo [9.5.1.1$^{3,9}$.1$^{5,15}$.1$^{7,13}$] octasiloxane-1-yl)propyl (meth) acrylate, 3-(3,5,7,9,11,13,15-heptaisooctylpentacyclo [9.5.1.1$^{3,9}$.1$^{5,15}$.1$^{7,13}$]-octasiloxane-1-yl)propyl (meth) acrylate, 3-(3,5,7,9,11,13,15-heptacyclopentylpentacyclo-[9.5.1.1$^{3,9}$.1$^{5,15}$.1$^{7,13}$] octasiloxane-1-yl)propyl (meth) acrylate, 3-(3,5,7,9,11,13,15-heptaphenylpentacyclo [9.5.1.1$^{3,9}$.1$^{5,15}$.1$^{7,13}$]-octasiloxane-1-yl)propyl (meth) acrylate, 3-[(3,5,7,9,11,13,15-heptaethylpentacyclo-[9.5.1.1$^{3,9}$.1$^{5,15}$.1$^{7,13}$] octasiloxane-1-yloxy)dimethylsilyl] propyl (meth)acrylate, 3-[(3,5,7,9,11,13,15-heptaisobutylpentacyclo-[9.5.1.1$^{3,9}$.1$^{5,15}$.1$^{7,13}$] octasiloxane-1-yloxy)dimethylsilyl]propyl (meth)acrylate, 3-[(3,5,7,9,11,13,15-heptaisooctylpentacyclo-[9.5.1.1$^{3,9}$.1$^{5,15}$.1$^{7,13}$] octasiloxane-1-yloxy)dimethylsilyl]propyl (meth)acrylate, 3-[(3,5,7,9,11,13,15-heptacyclopentylpentacyclo-[9.5.1.1$^{3,9}$.1$^{5,15}$.1$^{7,13}$] octasiloxane-1-yloxy)dimethylsilyl]propyl (meth)acrylate, 3-[(3,5,7,9,11,13,15-heptaphenylpentacyclo-[9.5.1.1$^{3,9}$.1$^{5,15}$.1$^{7,13}$] octasiloxane-1-yloxy)-dimethylsilyl]propyl (meth)acrylate, ethylene oxide adducts of (meth)acrylic acid, trifluoromethylmethyl (meth)acrylate, 2-trifluoromethylethyl (meth)acrylate, 2-perfluoroethylethyl (meth)acrylate, 2-perfluoroethyl-2-perfluorobutylethyl (meth)acrylate, 2-perfluoroethyl (meth)acrylate, trifluoromethyl (meth)acrylate, diperfluoromethylmethyl (meth)acrylate, 2-perfluoromethyl-2-perfluoroethylethyl (meth)acrylate, 2-perfluorohexylethyl (meth)acrylate, 2-perfluorodecylethyl (meth)acrylate, 2-perfluorohexadecylethyl (meth)acrylate, and the like.

Another example of the monofunctional monomer is a styrene base monomer. The specific examples thereof are styrene, vinyltoluene, α-methylstyrene, p-chlorostyrene, p-chloromethylstyrene, m-chloromethylstyrene, o-aminostyrene, p-styrenechlorosulfonic acid, styrenesulfonic acid and salts thereof, vinylphenylmethyl dithiocarbamate, 2-(2-bromopropanonyloxy)styrene, 2-(2-bromo-isobutyryloxy)styrene, 1-(2-((4-ethenylphenyl)-methoxy)-1-phenylethoxy)-2,2,6,6-tetramethyl-piperidine, 1-(4-vinylphenyl)-3,5,7,9,11,13,15-heptaethylpentacyclo-[9.5.1.1$^{3,9}$.1$^{5,15}$.1$^{7,13}$]-octasiloxane, 1-(4-vinylphenyl)-3,5,7,9,11,13,15-heptaisobutylpentacyclo[9.5.1.1$^{3,9}$.1$^{5,1}$.1$^{7,13}$]-octasiloxane, 1-(4-vinylphenyl)-3,5,7,9,11,13,15-heptaisooctylpentacyclo[9.5.1.1$^{3,9}$.1$^{5,15}$.1$^{7,13}$]-octasiloxane, 1-(4-vinylphenyl)-3,5,7,9,11,13,15-heptacyclopentylpentacyclo[9.5.1.1$^{3,9}$.1$^{5,15}$.1$^{7,13}$]-octasiloxane, 1-(4-vinylphenyl)-3,5,7,9,11,13,15-heptaphenylpentacyclo[9.5.1.1$^{3,9}$.1$^{5,15}$.1$^{7,13}$]-octasiloxane, 3-(3,5,7,9,11,13,15-heptaethylpentacyclo[9.5.1.1$^{3,9}$.1$^{5,15}$.1$^{7,13}$] octasiloxane-1-yl)ethylstyrene, 3-(3,5,7,9,11,13,15-heptaisobutylpentacyclo[9.5.1.1$^{3,9}$.1$^{5,15}$.1$^{7,13}$]-octasiloxane-1-yl)ethylstyrene, 3-(3,5,7,9,11,13,15-heptaisooctylpentacyclo[9.5.1.1$^{3,9}$.1$^{5,15}$.1$^{7,13}$]-octasiloxane-1-yl)ethylstyrene, 3-(3,5,7,9,11,13,15-heptacyclopentylpentacyclo[9.5.1.1$^{3,9}$.1$^{5,15}$.1$^{7,13}$]-octasiloxane-1-yl)ethylstyrene, 3-(3,5,7,9,11,13,15-heptaphenylpentacyclo[9.5.1.1$^{3,9}$.1$^{5,15}$.1$^{7,13}$]-octasiloxane-1-yl)ethylstyrene, 3-((3,5,7,9,11,13,15-heptaethylpentacyclo[9.5.1.1$^{3,9}$.1$^{5,15}$.1$^{7,13}$]octasiloxane-1-yloxy)dimethylsilyl]ethylstyrene, 3-((3,5,7,9,11,13,15-heptaisobutylpentacyclo-[9.5.1.1$^{3,9}$.1$^{5,15}$.1$^{7,13}$]octasiloxane-1-yloxy)dimethylsilyl)ethylstyrene, 3-((3,5,7,9,11,13,15-heptaisooctylpentacyclo-[9.5.1.1$^{3,9}$.1$^{5,15}$.1$^{7,13}$]octasiloxane-1-yloxy)-dimethylsilyl)ethylstyrene, 3-((3,5,7,9,11,13,15-heptacyclopentylpentacyclo[9.5.1.1$^{3,9}$.1$^{5,15}$.1$^{7,13}$]-octasiloxane-1-yloxy)dimethylsilyl)ethylstyrene, 3-((3,5,7,9,11,13,15-heptaphenylpentacyclo-[9.5.1.1$^{3,9}$.1$^{5,15}$.1$^{7,13}$] octasiloxane-1-yloxy)dimethylsilyl]ethylstyrene, and the like.

The examples of the other monofunctional monomers are fluorine-containing vinyl monomers (perfluoroethylene, perfluoropropylene, vinylidene fluoride and the like), silicon-containing vinyl base monomers (vinyltrimethoxysilane, vinyltriethoxysilane and the like), maleic anhydride, maleic acid, monoalkyl esters and dialkyl esters of maleic acid, fumaric acid, monoalkyl esters and dialkyl esters of fumaric acid, maleimide base monomers (maleimide, methylmaleimide, ethylmaleimide, propylmaleimide, butylmaleimide, hexylmaleimide, octylmaleimide, dodecylmaleimide, stearylmaleimide, phenylmaleimide and cyclohexylmaleimide), nitrile group-containing monomers (acrylonitrile, methacrylonitrile and the like), amide group-containing monomers (acrylamide, methacrylamide and the like), vinyl ester base monomers (vinyl acetate, vinyl propionate, vinyl pivalate, vinyl benzoate, vinyl cinnamate and the like), olefins (ethylene, propylene and the like), conjugated diene base monomers (butadiene, isoprene and the like), halogenated vinyls (vinyl chloride and the like), halogenated vinylidenes (vinylidene chloride and the like), halogenated allyls (allyl chloride and the like), allyl alcohol, vinylpyrrolidone, vinylpyridine, N-vinylcarbazole, methyl vinyl ketone, vinylisocyanate, and the like. Further, given as well are macromonomers which have one polymerizable double bond in a molecule and in which a principal chain is derived from styrene, (meth)acrylic acid ester and siloxane.

The examples of multifunctional monomers having two addition-polymerizable double bonds are 1,3-butanediol di(meth)acrylate, 1,4-butanediol di(meth)acrylate, 1,6-hexanediol di(meth)acrylate, polyethylene glycol di(meth)acrylate, diethylene glycol di(meth)acrylate, neopentyl glycol di(meth)acrylate, triethylene glycol di(meth)acrylate, tripropylene glycol di(meth)acrylate, hydroxypivalic acid ester neopentyl glycol di(meth)acrylate, trimethylolpropane di(meth)acrylate, bis[(meth)acryloyloxyethoxy] bisphenol A, bis[(meth)acryloyloxyethoxy] tetrabromobisphenol A, bis[(meth)acryloxypolyethoxy] bisphenol A, 1,3-bis(hydroxyethyl)-5,5-dimethylhydantoin, 3-methylpentanediol di(meth)acrylate, di(meth)acrylates of hydroxypivalic acid ester neopentyl glycol derivatives, bis[(meth)acryloyloxypropyl]-tetramethyldisiloxane, divinylbenzene, and the like. Further, given as well are macromonomers which have two polymerizable double bonds in a molecule and in which a principal chain is derived from styrene, (meth)acrylic acid ester and siloxane.

The examples of multifunctional monomers having three or more addition-polymerizable double bonds are trimethylolpropane tri(meth)acrylate, pentaerythritol tri(meth)acrylate, pentaerythritol tetra(meth)acrylate, dipentaerythritol monohydroxypenta(meth)acrylate, tris(2-hydroxyethyliso-cyanate) tri(meth)acrylate, tris(diethylene glycol)trimelate tri(meth)acrylate, 3,7,14-tris[(((meth)acryloyloxypropyl)-dimethylsiloxy)]-1,3,5,7,9,11,14-heptaethyltricyclo-[7.3.3.1$^{5,11}$]heptasiloxane, 3,7,14-tris[(((meth)acryloyloxypropyl)dimethylsiloxy)]-1,3,5,7,9,11,14-heptaisobutyltricyclo[7.3.3.1$^{5,11}$]-heptasiloxane, 3,7,14-tris[(((meth)acryloyloxy-propyl)dimethylsiloxy)]-1,3,5,7,9,11,14-heptaisooctyltricyclo[7.3.3.1$^{5,11}$]heptasiloxane, 3,7,14-tris[(((meth)acryloyloxypropyl)-dimethylsiloxy)]-1,3,5,7,9,11,14-heptacyclopentyl-tricyclo[7.3.3.1$^{5,11}$]heptasiloxane, 3,7,14-tris[(((meth)acryloyloxypropyl)dimethylsiloxy)]-1,3,5,7,9,11,14-heptaphenyltricyclo[7.3.3.1$^{5,11}$]-heptasiloxane, octakis(3-(meth)acryloyloxypropyl-dimethylsiloxy)octasilsesquioxane, octakis(3-(meth)acryloyloxypropyl)octasilsesquioxane, and the like. Further, given as well are macromonomers which have two or more polymerizable double bonds in a molecule and in which a principal chain is derived from styrene, (meth)acrylic acid ester and siloxane.

The monomers described above may be used alone or a plurality thereof may be copolymerized. When copolymerized, they may be random-copolymerized or block-copolymerized. The preferred monomers used in the present invention are the (meth)acrylic acid derivatives and the styrene derivatives. The more preferred monomers are the (meth)acrylic acid derivatives. The plural (meth)acrylic acid derivatives may be copolymerized, and the plural styrene derivatives may be copolymerized. At least one (meth)acrylic acid derivative may be copolymerized with at least one styrene derivative.

Next, a method for subjecting a vinyl base monomer to atom transfer radical polymerization using the compound (5) as an initiator and a transition metal complex as a catalyst shall be explained. The atom transfer radical polymerization in the present invention is one of living radical polymerizations, and it is a method for radically polymerizing a vinyl monomer using an organic halide or a halogenated sulfonyl compound as an initiator. This method is disclosed in J. Am. Chem. Soc., 1995, 117, 5614, Macromolecules, 1995, 28, 7901 and Science, 1996, 272, 866.

The preferred example of a transition metal complex used as a polymerizing catalyst is a metal complex in which the 7th, 8th, 9th, 10th or 11th group element in the periodic table is used as center metal. More preferred catalyst is a complex of zero-valent cupper, monovalent cupper, divalent ruthenium, divalent iron or divalent nickel. Among them, the complex of cupper is preferred. The examples of a monovalent copper compound are cuprous chloride, cuprous bromide, cuprous iodide, cuprous cyanide, cuprous oxide and cuprous perchlorate. When using the copper compounds, 2,2'-bipyridyl or derivatives thereof, 1,10-phenanthroline or derivatives thereof, pyridylmethaneimine (N-(n-propyl)-2-pyridylmethaneimine and the like), polyamine (tetramethylethylenediamine, pentamethyldiethylenetriamine, hexamethyltris(2-aminoethyl)amine and the like) or polycyclic alkaloid such as L-(−)-sparteine is added as a ligand in order to enhance the catalyst activity. A tristriphenylphosphine complex $(RuCl_2(PPh_3)_3)$ of divalent ruthenium chloride is also suited as the catalyst. When the ruthenium compound is used as the catalyst, aluminum alkoxides are added as an activating agent. Further, a bistriphenylphosphine complex $(FeCl_2(PPh_3)_2)$ of divalent iron, a bistriphenylphosphine complex $(NiCl_2(PPh_3)_2)$ of divalent nickel and a bistributylphosphine complex $(NiBr_2(PBu_3)_2)$ of divalent nickel are also suited as the catalyst.

A solvent may be used for the polymerization reaction. The examples of the solvent used are hydrocarbon base solvents (benzene, toluene and the like), ether base solvents (diethyl ether, tetrahydrofuran, diphenyl ether, anisole, dimethoxybenzene and the like), halogenated hydrocarbon base solvents (methylene chloride, chloroform, chlorobenzene and the like), ketone base solvents (acetone, methyl ethyl ketone, methyl isobutyl ketone and the like), alcohol base solvents (methanol, ethanol, propanol, isopropanol, n-butyl alcohol, tert-butyl alcohol and the like), nitrile base solvents (acetonitrile, propionitrile, benzonitrile and the like), ester base solvents (ethyl acetate, butyl acetate and the like), carbonate base solvents (ethylene carbonate, propylene carbonate and the like), amide base solvents (N,N-dimethylformamide, N,N-dimethylacetamide and the like), hydrochlorofluorocarbon base solvents (HCFC-141b, HCFC-225), hydrofluorocarbon base solvents (HFCs), perfluorocarbon base solvents (perfluoropentane, perfluorohexane), alicyclic hydrofluorocarbon base solvents (fluorocyclopentane, fluorocyclobutane), oxygen-containing fluorine base solvents (fluoroether, fluoropolyether fluoroketone, fluoroalcohol), water, and the like. They may be used alone or in combination of two or more kinds thereof. The polymerization can be carried out as well in an emulsion system or a system in which a supercritical fluid $CO_2$ is used as a medium. The solvent which can be used shall not be restricted to these examples.

The atom transfer radical polymerization can be carried out under reduced pressure, atmospheric pressure or applied pressure according to the kind of the vinyl monomer and the kind of the solvent. An organic metal complex used in combination or a radical produced is likely to be deactivated when brought into contact with oxygen. In such case, the polymerization rate is reduced, and a good living polymer is not obtained. Accordingly, it is important to carry out the polymerization under inert gas environment of nitrogen or argon. In this reaction, dissolved oxygen in the polymerization system has to be removed in advance under reduced pressure. It is possible to shift to a polymerization step as it is under reduced pressure after finishing the step of removing dissolved oxygen. The polymerization form of the atom transfer radical polymerization shall not specifically be restricted, and a conventional process, for example, bulk polymerization, solution polymerization, suspension polymerization, emulsion polymerization or bulk-suspension polymerization can be adopted. The polymerization temperature falls in a range of 0 to 200° C., and the preferred polymerization temperature falls in a range of a room temperature to 150° C.

Next, controlling of the structure of the compound (7) shall be explained. This compound is produced by the atom transfer radical polymerization method with the compound (5) being used as the initiator and the transition metal complex being used as the catalyst:

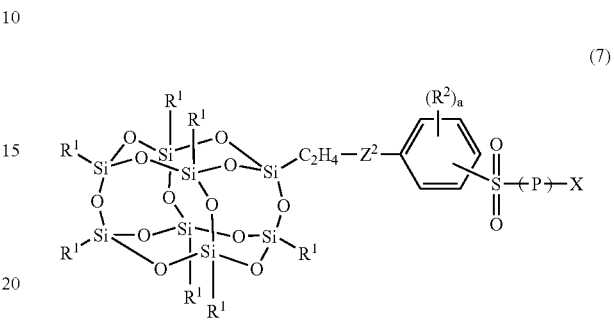

P in this formula is a vinyl polymer, and the other marks and the bonding positions of the substituents each are the same as these marks and bonding positions in Formula (5).

Suitable selection of the kind of the vinyl base monomer used makes it possible to control the structure of the compound (7) produced. For example, if the monomer is homopolymerized, silsesquioxane to which the homopolymer is bonded is obtained. If the plural monomers are added at the same time and polymerized, silsesquioxane to which the random copolymer is bonded is obtained. If used is a method in which the monomers are sequentially added, for example, a method in which the second monomer is added after finishing the polymerization of the first monomer to complete the polymerization, silsesquioxane to which a block copolymer is bonded is obtained. Repeating of this polymerization by stages using plural monomers makes it possible to obtain silsesquioxane to which a multiblock copolymer is bonded. A cross-linked polymer having a three-dimensional network structure can be prepared by allowing, if necessary, a multifunctional monomer to coexist.

Silsesquioxane to which a highly branched type polymer is bonded can be obtained by using in combination a compound (initiator-monomer) having an initiator and a polymerizable functional group altogether, for example, 2-2(bromopropionyloxy)ethyl (meth)acrylate, 2-2(bromoisobutyryloxy)ethyl (meth)acrylate, 2-2(bromopropionyloxy)styrene and 2-(2-bromoisobutyryloxy)styrene. Further, it is possible as well to positively introduce a silicon compound by using in combination trialkoxysilane, polydimethylsiloxane and silsesquioxane which have, for example, a (meth)acryl group and a styryl group as a polymerizable functional group. After copolymerized with a vinyl base monomer having an initiating group which does not take part in atom transfer radical polymerization, for example, 1-(2-((4-ethenylphenyl)methoxy)-1-phenylethoxy-2,2,6,6-tetramethylpyridine, 1-(meth)acryloxy-2-phenyl-2-(2,2,6,6-tetramethylpiperidinyloxy)ethane, 1-(4-((4-(meth)acryloxy)ethoxyethyl)phenylethoxy)piperidine or vinylphenylmethyldithiocarbamate, a vinyl base monomer is further polymerized in the other polymerization mode (for example, nitroxyl polymerization and photo initiator-transfer agent-terminator polymerization) using the resulting polymer as an initiator, whereby a graft copolymer can be formed.

After copolymerized with a monomer having a glycidyl group, for example, glycidyl (meth)acrylate, a monomer having an oxetanyl group, for example, 3-ethyl-3-(meth) acryloyloxymethyloxetane and a monomer having dioxolane, for example, 4-(meth)acryloyloxymethyl-2-methyl-2-ethyl-1,3-dioxolane, an aliphatic sulfonium salt, an aromatic sulfonium salt or an aromatic iodonium salt as a thermally latent or optically latent cation polymerization initiator is added to the resulting polymer, whereby a cross-linked polymer having a three-dimensional network structure can be prepared by cation polymerization. The examples of the aliphatic sulfonium salt which is the thermally latent cation polymerization initiator are 3-methyl-2-butenyltetramethylenesulfonium hexafluoroantimonate (Adeka Opton CP-77, commercial product manufactured by Asahi Denka Co., Ltd.) and 2-butenyltetramethylenesulfonium hexafluoroantimonate (Adeka Opton CP-66, commercial product manufactured by Asahi Denka Co., Ltd.), and the examples of the aromatic sulfonium salt which is the thermally or optically latent cation polymerization initiator are Sun Aid SI-15, SI-20, SI-25, SI-40, SI-45, SI-47, SI-60, SI-60L, SI-80, SI-80L, SI-100, SI-100L, SI-145, SI-150 and SI-160 (all are commercial products manufactured by Sanshin Chemical Industry Co., Ltd.), Adeka Optomer SP-172 and Adeka Optomer SP-152 (all are commercial products manufactured by Asahi Denka Co., Ltd.) and diphenyl-4-thiophenoxyphenylsulfonium hexafluoroantimonate. The example of the aromatic iodonium salt is (4-pentadecyloxyphenyl)-phenyliodonium hexafluoroantimonate. When carrying out optically latent cation polymerization, a photosensitizer, for example, Adeka Optomer SP-100 (commercial product manufactured by Asahi Denka Co., Ltd.) may be used in combination. Also, when obtaining a cross-linked polymer having a three-dimensional network structure by cation polymerization, a monofunctional or multifunctional glycidyl base cross-linking agent or a monofunctional or multifunctional oxetane base cross-linking agent may be allowed to coexist.

Next, a refining method for the compound (7) shall be explained. This compound is isolated and refined by efficiently removing the unreacted vinyl base monomer. Various methods are available, and a refining method by reprecipitation operation is preferred. This refining method is carried out in the following manner. First, a solvent which does not dissolve the compound (7) but dissolves the unreacted vinyl monomer, a so-called precipitant is added to a polymerization reaction liquid containing the compound (7) and the unreacted vinyl monomer to precipitate only the compound (7). The preferred use amount of the precipitant is 20 to 50 times based on the weight of the polymerization reaction liquid containing the compound (7) and the unreacted vinyl monomer.

The preferred precipitant is a solvent which is compatible with the polymerization solvent and which does not dissolve the compound (7) at all but dissolves only the unreacted vinyl monomer and which has a relatively low boiling point. The examples of the preferred precipitant are lower alcohols or aliphatic hydrocarbons. The particularly preferred precipitant is hexane. A repeating frequency of the reprecipitation operation is advisably increased in order to further raise a removing efficiency of the unreacted monomer. This method makes it possible to deposit only the compound (7) in the poor solvent, and the polymer can readily be separated from the unreacted monomer by filtering operation.

The transition metal complex which is the polymerizing catalyst remains in the compound (7) isolated by the method described above, and therefore problems such as coloring of the polymer, influence on the physical properties and environmental safety are brought about in a certain case. Accordingly, this catalyst residue has to be removed in finishing the polymerization reaction. The catalyst residue can be removed by adsorbing treatment using activated carbon. The examples of adsorbents other than activated carbon are ion exchange resins (acid, basic or chelate form) and inorganic adsorbents. The inorganic adsorbent has a character of a solid acid, a solid base or neutrality. This is a particle having a porous structure and therefore has a very high adsorbing ability. It is also one of the characteristics of the inorganic adsorbent that it can be used in a wide temperature range extending from a low temperature to a high temperature.

The examples of the inorganic adsorbent are silicon dioxide, magnesium oxide, silica-alumina, aluminum silicate, activated alumina, clay base adsorbents such as acid clay and activated clay, zeolite base adsorbents, dawsonites compounds and hydrotalcites compounds. Zeolite includes natural products and synthetic products, and both can be used. Kinds such as a crystal form, an amorphous form, a noncrystal form, a glass form, a synthetic product and a natural product are available for silicon dioxide, and silicon dioxide of a powder form can be used in the present invention regardless of the kind. The examples of natural aluminum silicate are pumice, fly ash, kaoline, bentonite, activated clay and diatomaceous earth. Synthetic aluminum silicate has a large specific surface area and a high adsorbing ability. The hydrotalcites compound is carbonate hydrate of aluminum-magnesium hydroxide.

The acid adsorbent and the basic adsorbent are preferably used in combination with activated carbon. The examples of the acid adsorbent are acid clay, activated clay, aluminum silicate, and the like. The examples of the basic adsorbent are activated alumina, the zeolite base adsorbents, the hydrotalcites compounds each described above, and the like. These adsorbents may be used alone or in a mixture of two or more kinds thereof. The compound (7) produced by the atom transfer radical polymerization can be refined by bringing into contact with activated alumina. A commercial product available from Aldrich Co., Ltd. can be used as activated alumina. When adsorbing treatment is carried out by using activated alumina in combination with the other adsorbent, the adsorbents can be mixed and brought into contact with the compound, but they may be brought into contact at the separate steps respectively. When brought into contact with the adsorbent, the reaction liquid may be used as it is or may be diluted with a solvent. The diluent may be selected from usual solvents on the condition that only a poor solvent for the polymer is not used. A temperature for treating with the adsorbent shall not specifically be restricted. The treatment may be carried out usually at 0 to 200° C. The preferred temperature range is a room temperature to 180° C. A use amount of the absorbent falls in a range of 0.1 to 500% by weight based on the weight of the compound (7). Considering the economical efficiency and the operability, the preferred range is 0.5 to 10% by weight.

A method of a batch system in which stirring-mixing and solid-liquid separation are carried out by batch operation can be used for solid-liquid contact of the absorbent and the polymer liquid. In addition thereto, capable of being used is a method of a continuous system such as a fixed layer system in which the polymer liquid is passed through a vessel charged with the adsorbent, a moving layer system in which the liquid is passed through a moving layer of the adsorbent and a fluidized layer system in which the adsorbent is fluidized by a liquid to carry out adsorption. Further, mixing and dispersing operation carried out by stirring can be combined, if necessary, with operation for elevating the dispersing efficiency, such as shaking of the vessel and use of a supersonic wave. After the polymer liquid is brought into contact with the absorbent, the absorbent is removed by filtering, centrifugal separation and settling separation, and washing treatment is carried out if necessary to obtain the refined polymer liquid. Treatment by the absorbent is carried out for the polymer (7) which is the final product, and it may be carried out for an intermediate product used for producing this polymer. For example, in the respective polymerizing steps of the block copolymer obtained by the atom transfer radical polymerization, this polymer can be isolated and subjected to adsorbing treatment. The polymer (7) subjected to treatment by the adsorbent may be separated by depositing in a poor solvent or distilling off volatile components such as the solvent under reduced pressure.

The analytical methods of a molecular weight and a molecular weight distribution of the compound (7) produced shall be explained. Usually, a molecular weight of a vinyl polymer can be measured by gel permeation chromatography (GPC) using a calibration curve in which a linear polymer such as polystyrene and methyl (meth)acrylate is used as a standard sample. Accordingly, the molecular weight and the molecular weight distribution of the compound (7) produced can be analyzed by GPC.

The compound (7) has silsesquioxane at an end part thereof, and therefore it can readily be decomposed under an acid condition or a basic condition. That is, an accuracy of molecular weight analysis of a grown polymer chain can further be enhanced by cutting off a vinyl base polymer from silsesquioxane and then measuring the molecular weight thereof. Hydrofluoric acid is preferably used for decomposing the compound (7) if decomposed under an acid condition, and potassium hydroxide is preferably used if it is decomposed under a basic condition. The compound (7) can be decomposed in either of a homogeneous system and an emulsion system. For example, the silsesquioxane part of the compound (7) can be decomposed in a mixed system of an organic solvent (tetrahydrofuran, acetonitrile and the like) which can dissolve the compound (7) and hydrofluoric acid. Further, the silsesquioxane part can be decomposed as well in an emulsion system, for example, a mixed system of toluene and hydrofluoric acid, and in this case, a phase transfer catalyst is preferably used in combination. When using potassium hydroxide, it can be decomposed as well in a mixed solvent of tetrahydrofuran, ethanol and water.

The vinyl polymer cut off by these methods is measured by GPC, whereby a molecular weight of the vinyl polymer contained in the compound (7) can be determined. It is possible as well to determine a molecular weight of the compound (7) by using a universal calibration curve obtained from the viscosity and the GPC data. An absolute molecular weight of the compound (7) can be determined as well by an end group determination method, a membrane osmotic pressure method, an ultracentrifuge method and a light scattering method.

A preferred molecular weight of the compound (7) falls in a range of 500 to 1,000,000 in terms of a number average molecular weight calculated in terms of polymethyl (meth) acrylate. The more preferred range is 1,000 to 100,000. However, the upper limit value and the lower limit value in this range do not necessarily have a specific meaning. The molecular weight distribution falls preferably in a range of 1.01 to 2.0 in terms of a dispersion degree (Mw/Mn).

The molecular weight of the compound (7) can be controlled by a proportion of the vinyl monomer to the compound (5) which is an initiator. That is, a theoretical molecular weight of the compound (7) can be predicted from a mole ratio of the vinyl monomer/compound (5) and a consumption rate of the monomer using the following calculation equation:

$$Mn = (\text{consumption rate (mole \%) of monomer}/100) \times MW_M \times (\text{mole ratio of vinyl base monomer/compound}(5)) + MW_I$$

In this calculation equation, Mn is a theoretical number average molecular weight; $MW_M$ is a molecular weight of the vinyl base monomer; and $MW_I$ is a molecular weight of the compound (5).

When obtaining a polymer having the number average molecular weight range described above, a mole ratio of the vinyl base monomer/halogenated alkylphenyl group can be selected from a range of about 2/1 to about 40000/1, preferably about 10/1 to about 5000/1. This number average molecular weight can be controlled by changing the polymerizing time. Any method of GPC, $^1$H-NMR and gas chromatography can be adopted as a method for determining a consumption rate (hereinafter referred to as "conversion rate") of the monomer.

The present invention shall more specifically be explained below with reference to examples, but the present invention shall not be restricted to the examples.

Codes used in the examples mean the following.
Ph: phenyl
CH: cyclohexyl
CP: cyclopentyl
Et: ethyl
iBu: isobutyl
iOc: isooctyl
TFPr: trifluoropropyl
TMS: trimethylsilyl
Mn: number average molecular weight
Mw: weight average molecular weight
Tg: glass transition temperature
Td: heat decomposition temperature Analytical conditions in Examples 1 to 30 are shown below.

<GPC>
Apparatus: JASCO GULLIVER 1500 (intelligent differential refractometer RI-1530), manufactured by JASCO Corp.
Solvent: tetrahydrofuran
Flow velocity: 1 ml/minute
Column temperature: 40° C.
Column used: TSKguardcolumn HXL-L (GUARDCOLUMN)+TSKgel G1000HxL (exclusion limiting molecular weight (polystyrene):1,000)+TSKgel G200HxL (exclusion limiting molecular weight (polystyrene):1,000)
Standard sample for calibration curve: Polymer Standards (PL), Polystyrene, manufactured by Polymer Laboratories Co., Ltd.

Analytical conditions in Examples 31 to 61 and Comparative Examples 1 to 7 are shown below.

<GPC>
Apparatus: 8020 Series (detector: differential refractometer), manufactured by Tosoh Corp.
Solvent: tetrahydrofuran
Flow velocity: 0.8 ml/minute
Column temperature: 40° C.

Column used: Shodex KF-LG (GUARDCOLUMN)+Shodex KF-804L (exclusion limiting molecular weight (polystyrene):400000)×2 columns
Standard sample for calibration curve: Polymer Standards (PL), Poly(methyl methacrylate), manufactured by Polymer Laboratories Co., Ltd.

<Tg>
Apparatus: differential scanning type calorimeter DSC7 (manufactured by Perkin-Elmer Co., Ltd.)
Heating rate: 10° C./minute
Measuring temperature range: 10 to 180° C.

<Td>
Apparatus: thermogravimetric apparatus TGA7 (manufactured by Perkin-Elmer Co., Ltd.)
Heating rate: 20° C./minute
Measuring temperature range: 50 to 800° C.

EXAMPLE 1

<Synthesis of Polyphenylsilsesquioxane (Compound A)>

A four neck separable flask having a content volume of 2 liter equipped with a reflux condenser, a thermometer and a dropping funnel was charged with ice and water (640.7 g) and toluene (200 g), and the inside of the flask was cooled to 0° C. while stirring. Next, a mixed solution of phenyltrichlorosilane (211.5 g) and toluene (130 g) dried on molecular sieves for a whole day and nigh was dropwise added thereto in one hour so that a temperature of the inside of the flask did not exceed 2° C. Then, after stirring at a room temperature for 30 minutes, the solution was washed with refined water, and toluene was distilled off under reduced pressure to obtain a solid compound A (120.7 g). The compound A had a weight average molecular weight of about 3100.

<Synthesis of Sodium-containing Phenylsilsesquioxane Compound (Compound B)>

A 500 ml-four neck flask equipped with a reflux condenser and a thermometer was charged with the compound A (12.9 g), tetrahydrofuran (250 ml) dried on molecular sieves for a whole day and night and sodium hydroxide (4.0 g), and the flask was heated at 67° C. while stirring by means of a magnetic stirrer to maintain a reflux state. After about 4 hours, the solution began to get cloudy by deposition of fine powder, and refluxing was continued for one hour as it was to finish the reaction. A solid matter deposited was washed with tetrahydrofuran and separated from tetrahydrofuran by filtering, and then it was dried under vacuum to obtain a compound B (10.1 g).

EXAMPLE 2

<Introduction of Trimethylsilyl Group into Compound B (Compound C)>

A four neck flask of 200 ml equipped with a reflux condenser was charged with the compound B (2.0 g) obtained in Example 1, toluene (100 g), triethylamine (1.7 g) and trimethylchlorosilane (1.4 g), and the mixture was stirred at a room temperature for 2 hours by means of a magnetic stirrer. After finishing the reaction, it was washed with refined water and dried under vacuum to obtain a compound C (2.1 g).

The compound C was subjected to structural analysis by means of $^1$H-NMR, $^{13}$C-NMR, $^{29}$Si-NMR, mass spectrometry, X ray crystal structure analysis and IR analysis. It was confirmed from a $^1$H-NMR chart and a $^{13}$C-NMR chart that a phenyl group and a trimethylsilyl group were present in an integral ratio of 7:3. It was confirmed from $^{29}$Si-NMR that three kinds of peaks of 11.547 ppm indicating a trimethylsilyl group, −77.574 ppm, −78.137 ppm and −78.424 ppm (all based on tetramethylsilane) having a phenyl group and indicating a T structure were present in a ratio of 1:3:3. It was confirmed from the measuring results of a mass spectrometric spectrum that the absolute molecular weight was consistent with a theoretical molecular weight of a structural body represented by Formula (9). It was confirmed from the measuring results of crystal structure analysis by X ray crystal structure analysis that the compound was the structural body represented by Formula (9). Confirmed from the measuring results of an IR absorption spectrum were absorptions assigned respectively to deformation vibration of Si—Ph in 1430 and 1590 cm$^{-1}$, harmonic vibration of a substituted benzene ring in 1960 to 1760 cm$^{-1}$, stretching vibration of Si—O—Si in 1200 to 950 cm$^{-1}$ and vibration of Si—CH$_3$ in 1250 cm$^{-1}$. These results support that the compound (compound C) replaced by a trimethylsilyl group has the structure represented by Formula (9), and this has made it apparent that the sodium-containing silsesquioxane compound (compound B) obtained has a structure represented by Formula (10). The T structure means a structure in which three oxygen atoms are bonded to an Si atom.

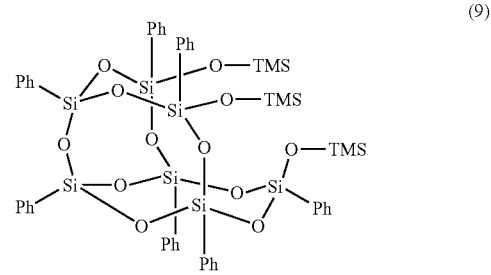

(9)

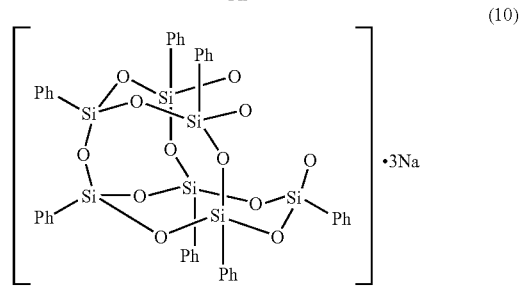

(10)

EXAMPLE 3

<Synthesis of Sodium-containing Phenylsilsesquioxane Compound (Compound B) Using Phenyltrimethoxysilane as Raw Material>

A four neck flask having a content volume of one liter equipped with a reflux condenser, a thermometer and a dropping funnel was charged with phenyltrimethoxyosilane (99 g), sodium hydroxide (10 g) and 2-propanol (500 ml), and a stirrer bar was put thereinto. Deionized water 11 g was dropwise added thereto from the dropping funnel in about 2 minutes while stirring at a room temperature by means of a magnetic stirrer, and then the flask was heated on an oil bath up to a temperature at which 2-propanol was refluxed. After refluxing was started, stirring was continued for 1.5 hour to complete the reaction. Then, the flask was pulled up from the oil bath and left standing still a night at a room temperature to completely deposit a solid matter produced. The solid matter deposited was filtrated by means of a pressure filter equipped with a membrane filter having a pore diameter of 0.1 µm. Then, the solid matter thus obtained was washed once with 2-propanol and dried at 70° C. for 4 hours in a vacuum dryer to obtain a compound B (66 g) of a white solid.

EXAMPLE 4

<Introduction of Trimethylsilyl Group into Compound B Obtained Using Phenyltrimethoxysilane as Raw Material (Compound C)>

A four neck flask having a content volume of 50 ml equipped with a dropping funnel, a reflux condenser and a thermometer was charged with a stirrer bar, the compound B (1.2 g) obtained in Example 3, tetrahydrofuran (12 g) and triethylamine (1.8 g), and the flask was sealed with dry nitrogen. Chlorotrimethylosilane (2.3 g) was dropwise added thereto from the dropping funnel at a room temperature in about one minute while stirring by means of a magnetic stirrer. After finishing dropwise adding, stirring was continued at a room temperature for 3 hours to complete the reaction. Then, 10 g of purified water was added thereto to hydrolyze sodium chloride produced and unreacted chlorotrimethylsilane. The reaction mixture thus obtained was transferred to a separating funnel and separated into an organic phase and an aqueous phase, and the resulting organic phase was repeatedly washed with deionized water until a washing liquid became neutral. The organic phase thus obtained was dried on anhydrous magnesium sulfate, filtered and concentrated under reduced pressure by means of a rotary evaporator to obtain a compound C (1.2 g) of a white solid.

The compound C was subjected to structural analysis by means of $^1$H-NMR, $^{13}$C-NMR, $^{29}$Si-NMR, mass spectrometry, X ray crystal structure analysis and IR analysis. It was confirmed from a $^1$H-NMR chart and a $^{13}$C-NMR chart that a phenyl group and a trimethylsilyl group were present in an integral ratio of 7:3. It was confirmed from $^{29}$Si-NMR that three kinds of peaks of 11.547 ppm indicating a trimethylsilyl group, -77.574 ppm, -78.137 ppm and -78.424 ppm (all based on tetramethylsilane) having a phenyl group and indicating a T structure were present in a ratio of 1:3:3. It was confirmed from the measuring results of a mass spectrometric spectrum that the absolute molecular weight was consistent with a theoretical molecular weight of the structure represented by Formula (9) described above. It was confirmed from the measuring results of crystal structure analysis by X ray crystal structure analysis that the compound was the structural body represented by Formula (9) described above. Confirmed from the measuring results of an IR absorption spectrum were absorptions assigned respectively to deformation vibration of Si—Ph in 1430 and 1590 cm$^{-1}$, harmonic vibration of a substituted benzene ring in 1960 to 1760 cm$^{-1}$, stretching vibration of Si—O—Si in 1200 to 950 cm$^{-1}$ and vibration of Si—CH$_3$ in 1250 cm$^{-1}$. These results support that the compound (compound C) replaced by a trimethylsilyl group has the structure represented by Formula (9) described above, and this has made it apparent that the sodium-containing silsesquioxane compound (compound B) obtained has the structure represented by Formula (10) described above. The T structure means a structure in which three oxygen atoms are bonded to an Si atom.

EXAMPLE 5

<Synthesis of Sodium-containing Cyclohexylsilsesquioxane Compound Using Cyclohexyltrimethoxysilane as Raw Material>

The same operation as in Example 3 is carried out, except that cyclohexyltrimethoxysilane is substituted for phenyltrimethoxyosilane, whereby a sodium-containing cyclohexylsilsesquioxane compound represented by Formula (11) can be obtained.

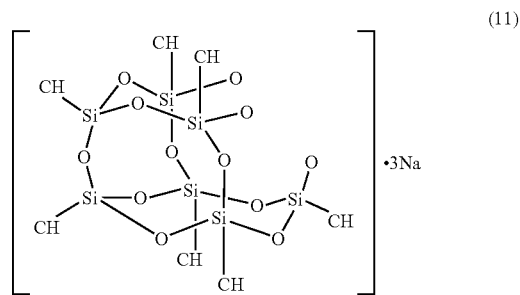

EXAMPLE 6

<Introduction of Trimethylsilyl Group into Compound (11)>

The same operation as in Example 4 is carried out, except that the compound (11) is substituted for the compound (10), whereby a trimethylsilyl group-containing cyclohexylsilsesquioxane compound represented by Formula (12) can be obtained. Further, it can be confirmed by subjecting the compound (12) to structural analysis by the same operation as in Example 4 that the compound (11) described above is produced.

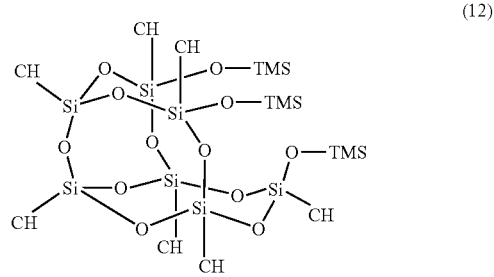

EXAMPLE 7

<Synthesis of Sodium-containing Cyclopentylsilsesquioxane Compound Using Cyclopentyltrimethoxysilane as Raw Material>

A four neck flask having a content volume of 200 ml equipped with a reflux condenser, a thermometer and a dropping funnel was charged with cyclopentyltrimethoxyosilane (19.0 g), THF (100 ml), sodium hydroxide (1.7 g) and deionized water (2.3 g), and the flask was heated while stirring by means of a magnetic stirrer. After refluxing was started at 67° C., stirring was continued for 10 hours to finish the reaction. Then, the flask was pulled up from the oil bath and left standing still a night at a room temperature to completely deposit a solid matter produced. The solid matter deposited was filtrated and dried under vacuum to obtain a compound of a powder-like solid (4.2 g).

EXAMPLE 8

<Introduction of Trimethylsilyl Group>

A four neck flask having a content volume of 100 ml equipped with a reflux condenser was charged with the compound (1.0 g) obtained in Example 7, THF (30 ml), triethylamine (0.5 g) and trimethylchlorosilane (0.7 g), and the mixture was stirred at a room temperature for 2 hours while stirring by means of a magnetic stirrer. After finishing the reaction, the same treatment as in confirming the structure in Example 4 was carried out to obtain a compound of a powder-like solid (0.9 g).

The compound thus obtained was analyzed by means of $^1$H-NMR, $^{29}$Si-NMR and X ray crystal structure analysis. It was confirmed from $^1$H-NMR that a cyclopentyl group and a trimethylsilyl group were present in an integral ratio of 7:3. Confirmed from $^{29}$Si-NMR were 8.43 ppm indicating a trimethylsilyl group and three kinds of peaks of −66.37 ppm, −67.97 ppm and −67.99 ppm having a cyclopentyl group and indicating a T structure. A ratio of the sum of the peak intensities of −67.97 ppm and −67.99 ppm to a peak intensity of −66.37 ppm was 6:1. It was confirmed from these results and the crystal structure obtained by the X ray crystal structure analysis that the compound of a powder-like solid matter which was the object of the analysis was a silicon compound represented by Formula (13). Accordingly, it was indicated that the compound obtained in Example 7 had a structure represented by Formula (14).

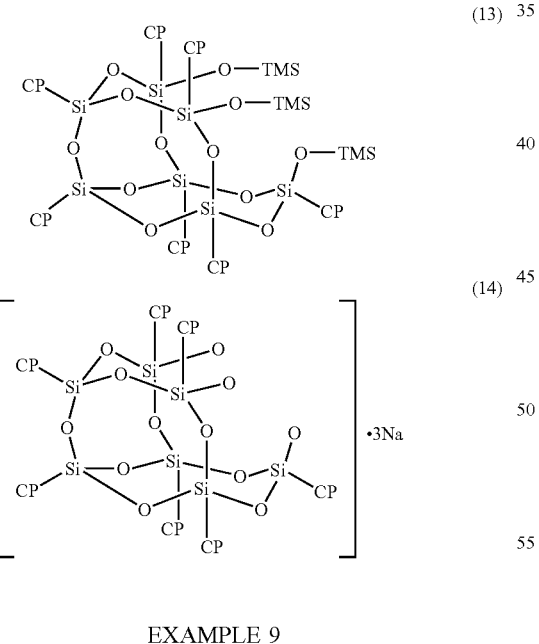

EXAMPLE 9

<Synthesis of Sodium-containing Ethylsilsesquioxane Compound Using Ethyltrimethoxysilane as Raw Material>

The same operation as in Example 3 is carried out, except that ethyltrimethoxysilane is substituted for phenyltrimethoxyosilane, whereby a sodium-containing ethylsilsesquioxane compound represented by Formula (15) can be obtained.

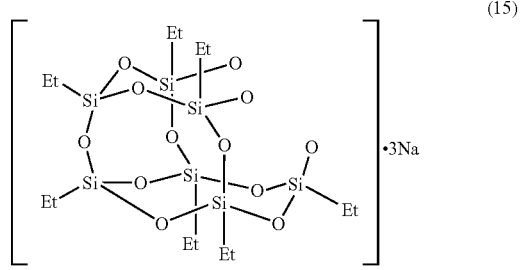

EXAMPLE 10

<Introduction of Trimethylsilyl Group into Compound (15)>

The same operation as in Example 4 is carried out, except that the compound (15) is substituted for the compound (10), whereby a trimethylsilyl group-containing ethylsilsesquioxane compound represented by Formula (16) can be obtained. Further, it can be confirmed by subjecting the compound (16) to structural analysis by the same operation as in Example 4 that the compound (15) described above is produced.

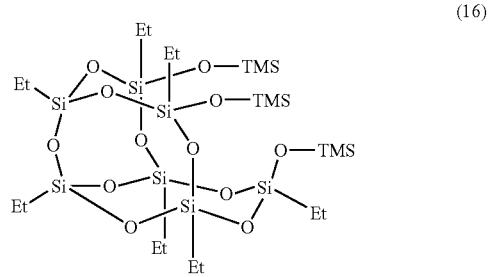

EXAMPLE 11

<Synthesis of Sodium-containing Isobutylsilsesquioxane Compound Using Isobutyltrimethoxysilane as Raw Material>

A four neck flask having a content volume of 200 ml equipped with a reflux condenser, a thermometer and a dropping funnel was charged with isobutyltrimethoxyosilane (18.7 g), THF (100 ml), sodium hydroxide (1.8 g) and deionized water (2.4 g), and the flask was heated while stirring by means of a magnetic stirrer. After refluxing was started at 67° C., stirring was continued for 10 hours to finish the reaction. The reaction liquid was concentrated under constant pressure until a solid matter was deposited, and then the resulting concentrate was left standing still a night at a room temperature to completely deposit the solid matter. This was filtered and dried under vacuum to obtain a compound of a powder-like solid (5.1 g).

EXAMPLE 12

<Introduction of Trimethylsilyl Group>

A four neck flask having a content volume of 200 ml equipped with a reflux condenser was charged with the compound of a powder-like solid matter (1.0 g) obtained in Example 11, THF (20 ml), triethylamine (0.5 g) and trimethylchlorosilane (0.8 g), and the mixture was stirred at a room temperature for 2 hours while stirring by means of a magnetic stirrer. After finishing the reaction, the same treatment as in confirming the structure in Example 4 was carried out to obtain a compound of a powder-like solid matter (0.9 g).

The powder-like solid matter described above was subjected to structural analysis by means of $^1$H-NMR and $^{29}$Si-NMR. It was confirmed from a $^1$H-NMR chart that an isobutyl group and a trimethylsilyl group were present in an integral ratio of 7:3. It was confirmed from $^{29}$Si-NMR that three kinds of peaks of 8.72 ppm indicating a trimethylsilyl group, −67.38 ppm, −68.01 ppm and −68.37 ppm having an isobutyl group and indicating a T structure were present in a ratio of 1:3:3. It was confirmed from these results that the compound of a powder-like solid matter which was the object of the analysis was a silicon compound represented by Formula (17). Accordingly, it was indicated that the compound obtained in Example 11 had a structure represented by Formula (18).

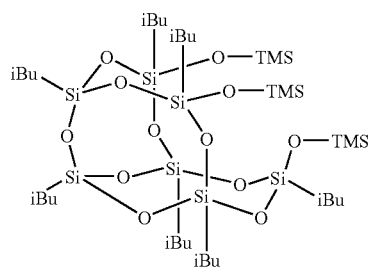
(17)

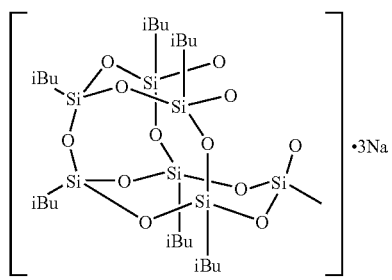
(18)

EXAMPLE 13

<Synthesis of Sodium-containing Isooctylsilsesquioxane>Compound Using Isooctyltrimethoxysilane as Raw Material The same operation as in Example 3 is carried out, except that isooctyltrimethoxysilane is substituted for phenyltrimethoxyosilane, whereby a sodium-containing isooctylsilsesquioxane compound represented by Formula (19) can be obtained.

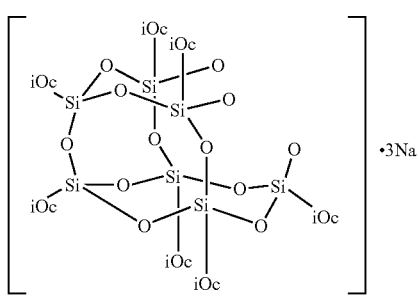
(19)

EXAMPLE 14

<Introduction of Trimethylsilyl Group into Compound (19)>

The same operation as in Example 4 is carried out, except that the compound (19) is substituted for the compound (10), whereby a trimethylsilyl group-containing isooctylsilsesquioxane compound represented by Formula (20) can be obtained. Further, it can be confirmed by subjecting the compound (20) to structural analysis by the same operation as in Example 4 that the compound (19) described above is produced.

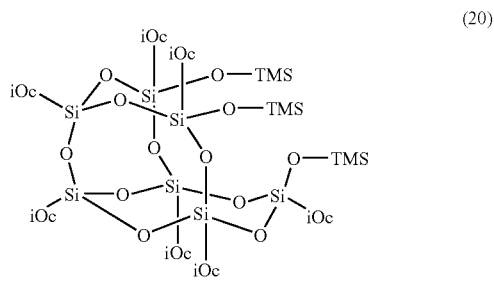
(20)

EXAMPLE 15

<Synthesis of Sodium-containing Trifluoropropylsilsesquioxane Compound Using Trifluoropropyltrimethoxysilane as Raw Material>

A four neck flask having a content volume of 1 liter equipped with a reflux condenser, a thermometer and a dropping funnel was charged with trifluoropropyltrimethoxyosilane (100 g), THF (500 ml), deionized water (10.5 g) and sodium hydroxide (7.9 g), and the flask was heated on an oil bath from a a room temperature up to a temperature at which THF was refluxed while stirring by means of a magnetic stirrer. After refluxing was started, stirring was continued for 5 hours to complete the reaction. Thereafter, the flask was pulled up from the oil bath and left standing still a night at a a room temperature, and then the flask was set again on the oil bath to heat and concentrate the reaction liquid under constant pressure until a solid matter was deposited. The product deposited was filtrated through a pressure filter equipped with a membrane filter having a pore diameter of 0.5 μm. Then, the solid matter thus obtained was washed once with THF and dried at 80 C for 3 hours in a vacuum dryer to obtain 74 g of a white power-like solid.

EXAMPLE 16

<Introduction of Trimethylsilyl Group>

A four neck flask having a content volume of 50 ml equipped with a dropping funnel, a reflux condenser and a thermometer was charged with the white power-like solid matter (1.0 g) obtained in Example 15, THF (10 g) and triethylamine (1.0 g), and the flask was sealed with dry nitrogen. Chlorotrimethylsilane (3.3 g) was dropwise added thereto at a room temperature in about one minute while stirring by means of a magnetic stirrer. After finishing dropwise adding, stirring was continued at a a room temperature for 3 hours to complete the reaction. Then, 10 g of purified water was added thereto to hydrolyze sodium chloride produced and unreacted chlorotrimethylsilane. The reaction mixture thus obtained was transferred to a separating funnel and separated into an organic phase and an aqueous phase, and the resulting organic phase was repeatedly washed with deionized water until a washing liquid became neutral. The organic phase thus obtained was dried on anhydrous magnesium sulfate, filtered and concentrated under reduced pressure by means of a rotary evaporator to obtain a compound (0.9 g) of a white solid.

The white powder-like solid obtained was subjected to structural analysis by means of GPC, $^1$H-NMR, $^{29}$Si-NMR and $^{13}$C-NMR. It was confirmed from a GPC chart that the white power-like solid matter showed a monodispersibility and had a weight average molecular weight of 1570 in terms of polystyrene and a purity of 98% by weight. It was confirmed from a $^1$H-NMR chart that a trifluoropropyl group and a trimethylsilyl group were present in an integral ratio of 7:3. It was confirmed from a $^{29}$Si-NMR chart that three kinds of peaks having a trifluoropropyl group and indicating a T structure were present in a ratio of 1:3:3 and that one peak indicating a trimethylsilyl group was present in 12.11 ppm. It was confirmed from a $^{13}$C-NMR chart that peaks indicating a trifluoropropyl group were present in 131 to 123 ppm, 28 to 27 ppm and 6 to 5 ppm and that a peak indicating a trimethylsilyl group was present in 1.4 ppm. These values show that the white power-like solid matter which is an object for the structural analysis has a structure of Formula (21). Accordingly, it is judged that the compound before trimethylsilylated has a structure of Formula (22).

compound B). Thereafter, the flask was stirred again in the ice bath for further one hour, and then the reaction liquid was filtered. The solvent was removed from the filtrate by means of a rotary evaporator to obtain a viscous liquid. Ethyl acetate (100 ml) was added to this viscous liquid, and then the liquid was concentrated by means of the rotary evaporator until it turned cloudy and left standing still as it was for 4 hours under an atmospheric pressure. Thereafter, filtration was carried out by means of a glass filter to obtain white crystal (1.16 g:yield 10%). This crystal was dissolved in orthodichlorobenzene and measured by gas chromatography, and as a result thereof, the presence of impurities was not confirmed. A single peak was confirmed as well from the result of GPC measurement, and the presence of the impurities was not confirmed. It was found from the results of IR, $^1$H-NMR, $^{13}$C-NMR and $^{29}$Si-NMR that the compound obtained had a structure represented by Formula (23).

IR: ν=1430 (Si-Ph), 1380, 1190 (—SO$_2$Cl), 1135 to 1090 (Si-Ph), 1090 to 1020 (Si—O—Si) cm$^{-1}$ $^1$H NMR (400 MHz, CDCl$_3$, TMS standard: δ=0.0 ppm): δ7.79 to 7.30 (m, 39H, Si—[C$_6$H$_5$], —[C$_6$H$_4$]—SO$_2$Cl), 2.91 (t, 2H, —[CH$_2$]—C$_6$H$_4$—), 1.23 (t, 2H, Si—[CH$_2$]—)

$^{13}$C NMR (100 MHz, CDCl$_3$, TMS standard: δ=0.0 ppm): 152.3, 142.0, 129.3, 127.2 (—[C$_6$H$_4$]—SO$_2$Cl), 134.3, 131.1, 130.2, 128.1 (Si—[C$_6$H$_5$]), 29.0 (—[CH$_2$]—C$_6$H$_4$—), 13.0 (Si—[CH$_2$]—)

$^{29}$Si NMR (CDCl$_3$, TMS standard: δ=0.0 ppm): −66.69 (—CH$_2$—[SiO$_{1.5}$]), −78.35, −78.41, −78.67 (C$_6$H$_5$—[SiO$_{1.5}$])

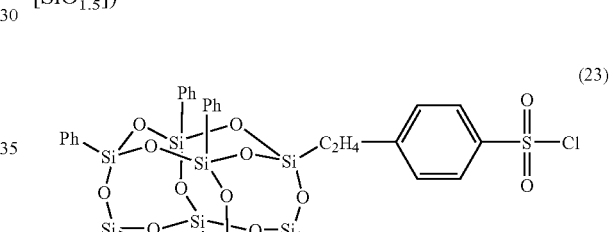

(23)

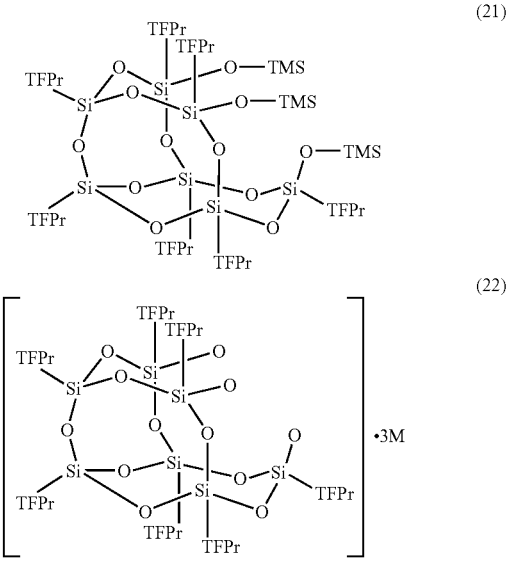

EXAMPLE 18

<Synthesis of 2-(4-chlorosulfonylphenyl)ethyl-heptacyclohexyloctasilsesquioxane Using the Compound (11) as Raw Material>

The same operation as in Example 17 is carried out, except that the compound (11) obtained in Example 5 is substituted for the compound (10), whereby a compound represented by Formula (24) can be obtained.

EXAMPLE 17

<Synthesis of 2-(4-chlorosulfonylphenyl)ethyl-heptaphenyloctasilsesquioxane Using the Compound (10) as Raw Material>

A 500 ml-four neck flask equipped with a dropping funnel, a reflux condenser, a thermometer and a rotator was set in an ice bath, and 10 g of the compound (10) obtained in Example 1 and tetrahydrofuran (200 ml) were introduced into this four neck flask. The flask was sufficiently cooled by liquid nitrogen, and then added thereto was a 2-(4-chlorosulfonylphenyl)ethyltrichlorosilane/methylene chloride solution (50 wt %) (10.17 g, 1.5 equivalent based on the

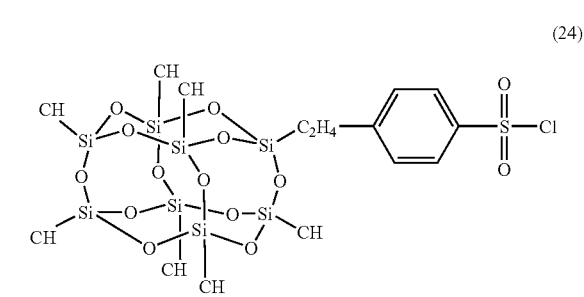

(24)

EXAMPLE 19

<Synthesis of 2-(4-chlorosulfonylphenyl)ethyl-heptacyclopentyloctasilsesquioxane Using the Compound (14) as Raw Material>

The same operation as in Example 17 is carried out, except that the compound (14) obtained in Example 7 is substituted for the compound (10), whereby a compound represented by Formula (25) can be obtained.

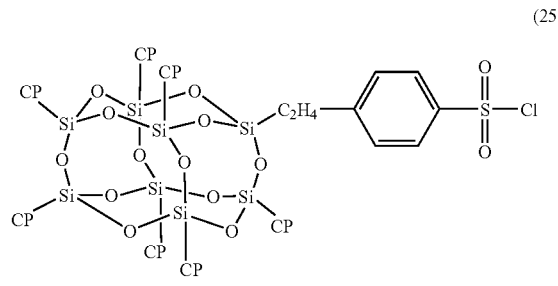
(25)

EXAMPLE 20

<Synthesis of 2-(4-chlorosulfonylphenyl)ethyl-heptaethyloctasilsesquioxane Using the Compound (15) as Raw Material>

The same operation as in Example 17 is carried out, except that the compound (15) obtained in Example 9 is substituted for the compound (10), whereby a compound represented by Formula (26) can be obtained.

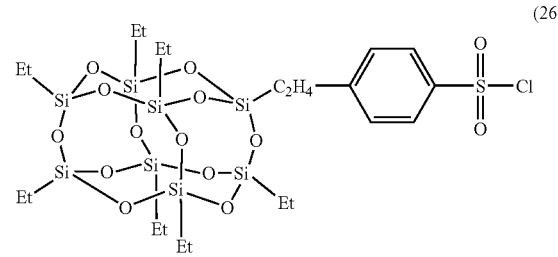
(26)

EXAMPLE 21

<Synthesis of 2-(4-chlorosulfonylphenyl)ethyl-heptaisobutyloctasilsesquioxane Using the Compound (18) as Raw Material>

The same operation as in Example 17 is carried out, except that the compound (18) obtained in Example 11 is substituted for the compound (10), whereby a compound represented by Formula (27) can be obtained.

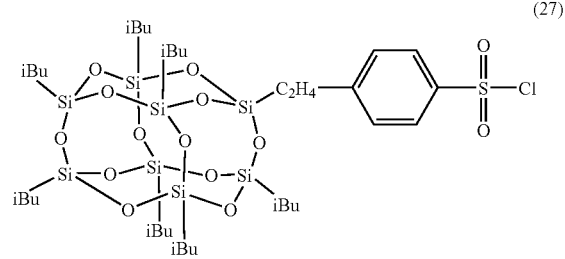
(27)

EXAMPLE 22

<Synthesis of 2-(4-chlorosulfonylphenyl)ethyl-heptaisooctyloctasilsesquioxane Using the Compound (19) as Raw Material>

The same operation as in Example 17 is carried out, except that the compound (19) obtained in Example 13 is substituted for the compound (10), whereby a compound represented by Formula (28) can be obtained.

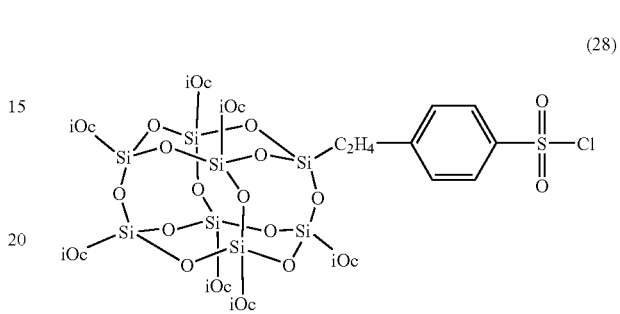
(28)

EXAMPLE 23

<Synthesis of 2-(4-chlorosulfonylphenyl)ethyl-heptatrifluoropropyloctasilsesquioxane Using the Compound (22) as Raw Material>

A 500 ml-four neck flask equipped with a dropping funnel, a reflux condenser, a thermometer and a rotator was set in an ice bath, and 11.37 g of the compound (22) obtained in Example 15, tetrahydrofuran (300 g) and triethylamine (1.5 g) were introduced into this four neck flask, and the mixture was stirred. Added thereto was a 2-(4-chlorosulfonylphenyl)ethyltrichlorosilane/methylene chloride solution (50 wt %) (10.14 g, 1.5 equivalent based on the compound (22)), and the mixture was stirred for 3 hours, followed by filtering the reaction liquid. The solvent was removed from the filtrate by means of a rotary evaporator to obtain a viscous liquid. Toluene was added to this viscous liquid, and then the liquid was concentrated by means of the rotary evaporator until it turned cloudy and left standing still as it was for 4 hours under an atmospheric pressure. This operation was repeated three times, and then the deposit was dissolved again in methylene chloride. Toluene was added thereto until the liquid turned cloudy, and it was left standing still in a refrigerator of −34° C. This operation was repeated twice, and then recrystallization was carried out from xylene to obtain colorless crystal (0.1 g: yield 0.77%) GPC measurement of this crystal was carried out to result in confirming a single peak, and the presence of impurities was not confirmed. It was found from the results of $^1$H-NMR, $^{13}$C-NMR and $^{29}$Si-NMR that the compound obtained had a structure represented by Formula (29).

$^1$H NMR (400 MHz, CDCl$_3$, TMS standard: δ=0.0 ppm): 7.98, 7.96, 7.45, 7.25 (s, 4H, —[C$_6$H$_4$]—SO$_2$Cl), 2.83 (t, 2H, —[CH$_2$]—C$_6$H$_4$—), 2.15 (m, 14H, —[CH$_2$]-CF$_3$), 1.10 (t, 2H, Si—[CH$_2$]—CH$_2$—C$_6$H$_4$—), 0.95 (m, 14H, Si—[CH$_2$]—CH$_2$—CF$_3$), $^{13}$C NMR (100 MHz, CDCl$_3$, TMS standard: δ=0.0 ppm): 151.9, 142.5, 129.0, 127.6 (—[C$_6$H$_4$]—SO$_2$Cl), 127.0 (—CH$_2$— [CF$_3$]), 28.9 (—[CH$_2$]—C$_6$H$_4$—), 27.9 (—[CH$_2$]—CF$_3$), 13.0 (Si—[CH$_2$]—CH$_2$—C$_6$H$_4$—), 4.0 (Si—[CH$_2$]-CH$_2$—CF$_3$)

$^{29}$Si NMR (CDCl$_3$, TMS standard: δ=0.0 ppm): −67.54 (—CH$_2$—[SiO$_{1.5}$]), −67.60, −67.62, −67.73 (C$_6$H$_5$—[SiO$_{1.5}$])

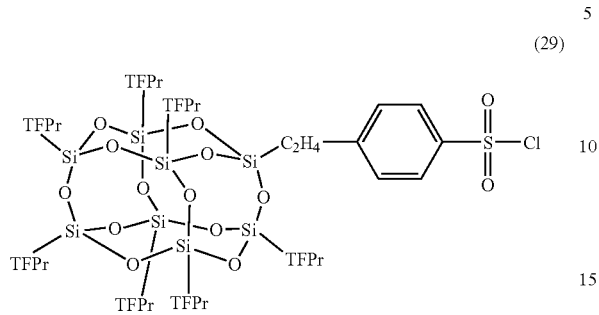

(29)

EXAMPLE 24

<Synthesis of 2-(4-chlorosulfonylphenyl)ethyl-heptaphenyloctasilsesquioxane Using the Compound (30) as Raw Material>

A compound represented by Formula (30) (10 g, trisilanolphenyl POSS, manufactured by Hybrid Plastics U.S Co., Ltd.), triethylamine (4.34 g, 1.3 equivalent based on silanol) and tetrahydrofuran (250 ml) were introduced into a 500 ml-four neck flask equipped with a dropping funnel, a reflux condenser, a thermometer and a rotator in an ice bath. Added thereto was a 2-(4-chlorosulfonylphenyl)ethyl-trichlorosilane/methylene chloride solution (50 wt %) (10.89 g, 1.5 equivalent based on the compound (30)), and the mixture was stirred at a room temperature for further one hour, followed by filtering the reaction liquid. The solvent was distilled off by means of a rotary evaporator to obtain a white viscous liquid. Ethyl acetate (100 ml) was added to the viscous liquid obtained, and then the liquid was concentrated by means of the rotary evaporator until it turned cloudy and left standing still as it was for 4 hours under an atmospheric pressure. Thereafter, filtration wad carried out by means of a glass filter (G3 grade) to obtain 1.28 g of colorless crystal (yield 10%). The compound obtained was dissolved (30.2 wt %) in orthodichlorobenzene and measured by gas chromatography, and as a result thereof, the presence of impurities was not confirmed. GPC measurement was carried out to result in confirming a single peak, and the presence of impurities was not confirmed. It was found from the results of IR, $^1$H-NMR, $^{13}$C-NMR and $^{29}$Si-NMR that the compound had a structure represented by Formula (23) shown in Example 17.

IR: ν=1430 (Si-Ph), 1380, 1190 (—SO$_2$Cl), 1135 to 1090 (Si-Ph), 1090 to 1020 (Si—O—Si) cm$^{-1}$ $^1$H NMR (400 MHz, CDCl$_3$, TMS standard: δ=0.0 ppm): δ7.79 to 7.30 (m, 39H, Si—[C$_6$H$_5$], —[C$_6$H$_4$]—SO$_2$Cl), 2.91 (t, 2H, —[CH$_2$]—C$_6$H$_4$—), 1.23 (t, 2H, Si—[CH$_2$]—)

$^{13}$C NMR (100 MHz, CDCl$_3$, TMS TMS standard: δ=0.0 ppm): 152.3, 142.0, 129.3, 127.2 (—[C$_6$H$_4$]—SO$_2$Cl), 134.3, 131.1, 130.2, 128.1 (Si—[C$_6$H$_5$]), 29.0 (—[CH$_2$]—C$_6$H$_4$—), 13.0 (Si—[CH$_2$]—)

$^{29}$Si NMR (CDCl$_3$, TMS standard: δ=0.0 ppm): −66.69 (—CH$_2$—[SiO$_{1.5}$]), −78.35, −78.41, −78.67 (C$_6$H$_5$—[SiO$_{1.5}$])

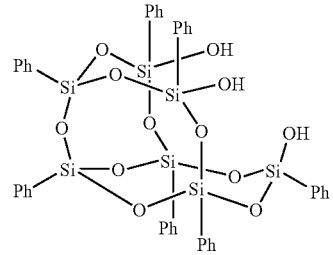

(30)

EXAMPLE 25

<Synthesis of 2-(4-chlorosulfonylphenyl)ethyl-heptacyclohexyloctasilsesquioxane Using the Compound (31) as Raw Material>

The same operation as in Example 24 is carried out, except that a compound represented by Formula (31) (trisilanolcyclohexyl POSS, manufactured by Hybrid Plastics U.S Co., Ltd.) is substituted for the compound (30), whereby the compound (24) described in Example 18 can be obtained.

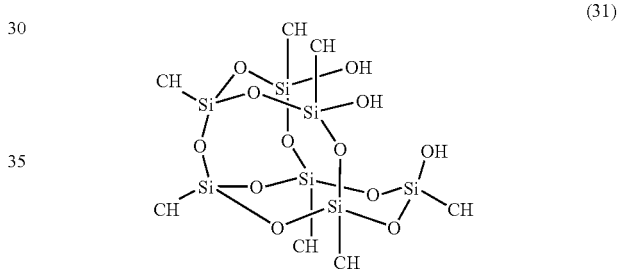

(31)

EXAMPLE 26

<Synthesis of 2-(4-chlorosulfonylphenyl)ethyl-heptacyclopentyloctasilsesquioxane Using the Compound (32) as Raw Material>

The same operation as in Example 24 is carried out, except that a compound represented by Formula (32) (trisilanolcyclopentyl POSS, manufactured by Hybrid Plastics U.S Co., Ltd.) is substituted for the compound (30), whereby the compound (25) described in Example 19 can be obtained.

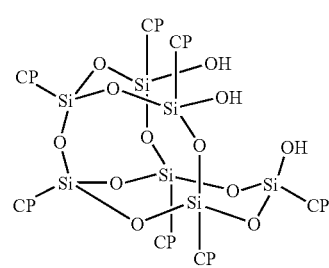

(32)

EXAMPLE 27

<Synthesis of 2-(4-chlorosulfonylphenyl)ethyl-heptaethyloctasilsesquioxane Using the Compound (33) as Raw Material>

The same operation as in Example 24 is carried out, except that a compound represented by Formula (33) (trisilanolethyl POSS, manufactured by Hybrid Plastics U.S Co., Ltd.) is substituted for the compound (30), whereby the compound (26) described in Example 20 can be obtained.

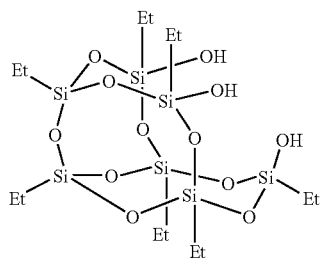

(33)

EXAMPLE 28

<Synthesis of 2-(4-chlorosulfonylphenyl)ethyl-heptaisobutyloctasilsesquioxane Using the Compound (34) as Raw Material>

The same operation as in Example 24 is carried out, except that a compound represented by Formula (34) (trisilanolisobutyl POSS, manufactured by Hybrid Plastics U.S Co., Ltd.) is substituted for the compound (30), whereby the compound (27) described in Example 21 can be obtained.

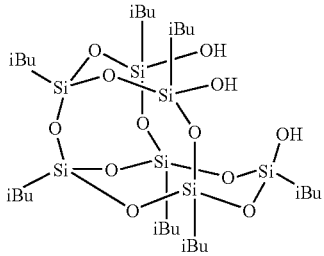

(34)

EXAMPLE 29

<Synthesis of 2-(4-chlorosulfonylphenyl)ethyl-heptaisooctyloctasilsesquioxane Using the Compound (35) as Raw Material>

The same operation as in Example 24 is carried out, except that a compound represented by Formula (35) (trisilanolisooctyl POSS, manufactured by Hybrid Plastics U.S Co., Ltd.) is substituted for the compound (30), whereby the compound (28) described in Example 22 can be obtained.

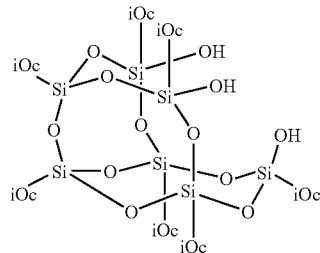

(35)

EXAMPLE 30

A 300 ml-four neck flask equipped with a dropping funnel, a reflux condenser, a thermometer and a rotator was set in an ice bath. The compound (22) 5 g obtained in Example 15 was added to this four neck flask and dissolved in butyl acetate (50 g), and then acetic acid (0.5 g) was dropwise added thereto. The flask was stirred for one hour as it was put in the ice bath. After returned to a room temperature, the reaction liquid was washed (three times) with deionized water (100 ml). The solvent was distilled off by means of a rotary evaporator and dried (50° C., one hour) as it was under reduced pressure to obtain a viscous liquid (4.3 g). GPC measurement of the compound obtained was carried out to result in showing a single peak, and the presence of impurities was not confirmed. Further, analysis using IR was carried out to result in confirming absorption (in the vicinity of 3400 cm$^{-1}$) indicating the presence of a silanol group which was not observed in the compound (22). Accordingly, it was indicated that the compound obtained had a structure represented by Formula (36).

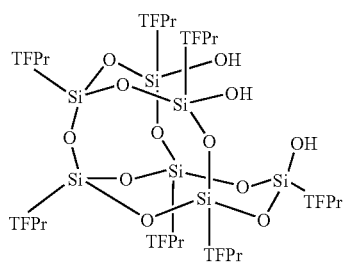

(36)

Chlorosulfonylphenylethyltrichlorosilane is reacted with the compound (36) described above which is a starting raw material under the presence of triethylamine according to the method described in Examples 24 to 29 described above, whereby the compound (29) can be derived.

EXAMPLE 31

<Preparation of Solution for Polymerization>

A compound (23)/methyl methacrylate/L-(−)-sparteine/anisole solution and cuprous bromide each were separately introduced into a feed forked heat resistant glass-made ampoule in a draft which was cut off from a UV ray. Then, freezing vacuum deaeration (pressure: 1.0 Pa) was carried out three times by means of a vacuum device equipped with an oil-sealed rotary pump while taking care so that both were not mixed. The compound (23)/methyl methacrylate/L-(−)-sparteine/anisole solution was mixed with cuprous bromide in the feed forked heat resistant glass-made ampoule while maintaining a vacuum state, and then the ampoule was quickly sealed by means of a hand burner. In this solution for polymerization, a proportion of the compound (23), methyl methacrylate, cuprous bromide and L-(−)-sparteine was set in this order to 1:500:2:4 in terms of a mole ratio, and a use amount of anisole was set to such an mount that a concentration of methyl methacrylate was 50 wt %.

<Polymerization>

The sealed heat resistant glass-made ampoule was set in a constant temperature shaking bath, and polymerization was carried out to obtain a brown viscous solution of a polymer (1a). In this case, the polymerization temperature was 70° C., and the polymerization time was 0.5 hour. Thereafter, the solution of the polymer (1a) was sampled and diluted with tetrahydrofuran, and then it was subjected to GPC measurement. A monomer conversion rate in this polymerization reaction system was analyzed based on a peak area obtained from a GPC measured value of a poly (methyl methacrylate) solution having a-known concentration. The analytical results of the monomer conversion rate and the molecular weight and the molecular weight distribution of the polymer (1a) are shown in Table 4.

EXAMPLE 32

Polymerization was carried out in the same manner as in Example 31 to obtain a brown viscous solution of a polymer (1b), except that the polymerization time was changed to one hour. The monomer conversion rate and a molecular weight and a molecular weight distribution of the polymer (1b) were determined in the same manner as in Example 31, and the results thereof are shown Table 4.

EXAMPLE 33

Polymerization was carried out in the same manner as in Example 31 to obtain a brown viscous solution of a polymer (1c), except that the polymerization time was changed to 2 hours. The monomer conversion rate and a molecular weight and a molecular weight distribution of the polymer (1c) were determined in the same manner as in Example 31, and the results thereof are shown Table 4.

EXAMPLE 34

Polymerization was carried out in the same manner as in Example 31 to obtain a brown viscous solution of a polymer (1d), except that the polymerization time was changed to 3 hours. The monomer-conversion rate and a molecular weight and a molecular weight distribution of the polymer (1d) were determined in the same manner as in Example 31, and the results thereof are shown Table 4.

EXAMPLE 35

Polymerization was carried out in the same manner as in Example 31 to obtain a brown viscous solution of a polymer (1e), except that the polymerization time was changed to 4 hours. The monomer conversion rate and a molecular weight and a molecular weight distribution of the polymer (1e) were determined in the same manner as in Example 31, and the results thereof are shown Table 4.

EXAMPLE 36

Polymerization was carried out in the same manner as in Example 31 to obtain a brown viscous solution of a polymer (1f), except that the polymerization time was changed to 14 hours. The monomer conversion rate and a molecular weight and a molecular weight distribution of the polymer (1f) were determined in the same manner as in Example 31, and the results thereof are shown Table 4.

EXAMPLE 37

<Preparation of Solution for Polymerization>

In this example, a proportion of the compound (23), methyl methacrylate, cuprous bromide and L-(−)-sparteine in the solution for polymerization was set in this order to 1:500:1:2 in terms of a mole ratio. Anisole was used so that a concentration of methyl methacrylate in the solution for polymerization was 50 wt %.

A compound (23)/methyl methacrylate/L-(−)-sparteine/anisole solution and cuprous bromide each were separately introduced into a feed forked heat resistant glass-made ampoule in a draft which was cut off from a UV ray. Then, freezing vacuum deaeration (pressure: 1.0 Pa) was carried out by means of the vacuum device equipped with an oil-sealed rotary pump while taking care so that both were not mixed. The frozen solution was molten at a room temperature, and dry argon gas was filled therein. The operation of carrying out freezing vacuum deaeration and filling of argon gas was repeated three times in total, and then the compound (23)/methyl methacrylate/L-(−)-sparteine/anisole solution was mixed with cuprous bromide in the feed forked heat resistant glass-made ampoule while maintaining a state of filling argon gas, followed by quickly sealing the ampoule by means of a hand burner.

<Polymerization>

The sealed heat resistant glass-made ampoule was set in a constant temperature shaking bath, and polymerization was carried out to obtain a brown viscous solution of a polymer (2a). In this case, the polymerization temperature was 70° C., and the polymerization time was one hour. Thereafter, the solution of the polymer (2a) was sampled and diluted with tetrahydrofuran, and then it was subjected to GPC measurement. A monomer conversion rate in this polymerization reaction system was determined from the relation of a proton ratio of substituents in the respective monomer and polymer by diluting the solution of the polymer (2a) with deuterated chloroform and then subjecting the solution to $^1$H-NMR. The results obtained by analyzing the monomer conversion rate and a molecular weight and a molecular weight distribution of the polymer (2a) are shown in Table 4.

EXAMPLE 38

Polymerization was carried out in the same manner as in Example 37 to obtain a brown viscous solution of a polymer (2b), except that the polymerization time was changed to 2 hours. The monomer conversion rate and a molecular weight and a molecular weight distribution of the polymer (2b) were determined in the same manner as in Example 37, and the results thereof are shown Table 4.

TABLE 4

| Example No. | Polymer No. | Conversion rate (mole-%) | Number average molecular weight (Mn) | Dispersion degree (Mw/Mn) |
|---|---|---|---|---|
| 31 | 1a | 6.51 | 3,000 | 1.11 |
| 32 | 1b | 8.42 | 4,300 | 1.11 |
| 33 | 1c | 16.7 | 9,400 | 1.10 |
| 34 | 1d | 18.9 | 13,500 | 1.09 |
| 35 | 1e | 34.3 | 20,600 | 1.11 |
| 36 | 1f | 67.3 | 39,600 | 1.13 |
| 37 | 2a | 4.4 | 3,800 | 1.15 |
| 38 | 2b | 8.2 | 4,200 | 1.12 |

EXAMPLE 39

<Preparation of Solution for Polymerization>

In this example, a proportion of the compound (23), methyl methacrylate, cuprous bromide and L-(−)-sparteine in the solution for polymerization was set in this order to 1:300:1:2 in terms of a mole ratio. Anisole was used so that a concentration of methyl methacrylate in the solution for polymerization was 50 wt %.

A compound (23)/methyl methacrylate/L-(−)-sparteine/anisole solution and cuprous bromide each were separately introduced into a feed forked heat resistant glass-made ampoule in a draft which was cut off from a UV ray. Then, freezing vacuum deaeration (pressure: 1.0 Pa) was carried out three times by means of the vacuum device equipped with an oil-sealed rotary pump while taking care so that both were not mixed. The compound (23)/methyl methacrylate/L-(−)-sparteine/anisole solution was mixed with cuprous bromide in the feed forked heat resistant glass-made ampoule while maintaining a state of vacuum, and then the ampoule was quickly sealed by means of a hand burner.

<Polymerization>

The sealed heat resistant glass-made ampoule was set in a constant temperature shaking bath, and polymerization was carried out to obtain a brown viscous solution of a polymer (3a). In this case, the polymerization temperature was 70° C., and the polymerization time was 2 hours. The monomer conversion rate and a molecular weight and a molecular weight distribution of the polymer (3a) were determined in the same manner as in Example 31, and the results thereof are shown in Table 5.

EXAMPLE 40

Polymerization was carried out in the same manner as in Example 39 to obtain a brown viscous solution of a polymer (3b), except that the polymerization time was changed to 4.2 hours. The monomer conversion rate and a molecular weight and a molecular weight distribution of the polymer (3b) were determined in the same manner as in Example 31, and the results thereof are shown Table 5.

EXAMPLE 41

Polymerization was carried out in the same manner as in Example 39 to obtain a brown viscous solution of a polymer (3c), except that the polymerization time was changed to 6.2 hours. The monomer conversion rate and a molecular weight and a molecular weight distribution of the polymer (3c) were determined in the same manner as in Example 31, and the results thereof are shown Table 5.

EXAMPLE 42

Polymerization was carried out in the same manner as in Example 39 to obtain a brown viscous solution of a polymer (3d), except that the polymerization time was changed to 9 hours. The monomer conversion rate and a molecular weight and a molecular weight distribution of the polymer (3d) were determined in the same manner as in Example 31, and the results thereof are shown Table 5.

EXAMPLE 43

Polymerization was carried out in the same manner as in Example 39 to obtain a brown viscous solution of a polymer (3e), except that the polymerization time was changed to 12 hours. The monomer conversion rate and a molecular weight and a molecular weight distribution of the polymer (3e) were determined in the same manner as in Example 31, and the results thereof are shown Table 5.

EXAMPLE 44

Polymerization was carried out in the same manner as in Example 39 to obtain a brown viscous solution of a polymer (3f), except that the polymerization time was changed to 20 hours. The monomer conversion rate and a molecular weight and a molecular weight distribution of the polymer (3f) were determined in the same manner as in Example 31, and the results thereof are shown Table 5.

EXAMPLE 45

Polymerization was carried out in the same manner as in Example 39 to obtain a brown viscous solution of a polymer (3g), except that the polymerization time was changed to 6 hours. The monomer conversion rate and a molecular weight and a molecular weight distribution of the polymer (3g) were determined in the same manner as in Example 31, and the results thereof are shown Table 5.

EXAMPLE 46

Polymerization was carried out in the same manner as in Example 39 to obtain a brown viscous solution of a polymer (3h), except that the polymerization time was changed to 8.5 hours. The monomer conversion rate and a molecular weight and a molecular weight distribution of the polymer (3h) were determined in the same manner as in Example 31, and the results thereof are shown Table 5.

EXAMPLE 47

Polymerization was carried out in the same manner as in Example 39 to obtain a brown viscous solution of a polymer (3i), except that the polymerization time was changed to 11 hours. The monomer conversion rate and a molecular weight and a molecular weight distribution of the polymer (3i) were determined in the same manner as in Example 31, and the results thereof are shown Table 5.

EXAMPLE 48

<Preparation of Solution for Polymerization>

In this example, a proportion of the compound (23), methyl methacrylate, cuprous bromide and L-(−)-sparteine in the solution for polymerization was set in this order to 1:3:002:4 in terms of a mole ratio. Anisole was used so that a concentration of methyl methacrylate in the solution for polymerization was 50 wt %.

A compound (23)/methyl methacrylate/L-(-)-sparteine/ anisole solution and cuprous bromide each were separately introduced into a feed forked heat resistant glass-made ampoule in a draft which was cut off from a UV ray. Then, freezing vacuum deaeration (pressure: 1.0 Pa) was carried out three times by means of the vacuum device equipped with an oil-sealed rotary pump while taking care so that both were not mixed. The silicon compound/methyl methacrylate/L-(-)-sparteine/anisole solution was mixed with cuprous bromide in the feed forked heat resistant glass-made ampoule while maintaining a state of vacuum, and then the ampoule was quickly sealed by means of a hand burner.

<Polymerization>

The sealed heat resistant glass-made ampoule was set in a constant temperature shaking bath, and polymerization was carried out to obtain a brown viscous solution of a polymer (4a). In this case, the polymerization temperature was 70° C., and the polymerization time was 2 hours. The monomer conversion rate and a molecular weight and a molecular weight distribution of the polymer (4a) were determined in the same manner as in Example 31, and the results thereof are shown in Table 5.

EXAMPLE 49

Polymerization was carried out in the same manner as in Example 48 to obtain a brown viscous solution of a polymer (4b), except that the polymerization time was changed to 4 hours. The monomer conversion rate and a molecular weight and a molecular weight distribution of the polymer (4b) were determined in the same manner as in Example 31, and the results thereof are shown Table 5.

TABLE 5

| Example No. | Polymer No. | Conversion rate (mole-%) | Number average molecular weight (Mn) | Dispersion degree (Mw/Mn) |
| --- | --- | --- | --- | --- |
| 39 | 3a | 10.1 | 2,600 | 1.10 |
| 40 | 3b | 14.4 | 4,700 | 1.08 |
| 41 | 3c | 16.6 | 6,500 | 1.07 |
| 42 | 3d | 22.8 | 10,900 | 1.07 |
| 43 | 3e | 27.9 | 13,200 | 1.08 |
| 44 | 3f | 39.9 | 18,400 | 1.10 |
| 45 | 3g | 34.7 | 13,500 | 1.07 |
| 46 | 3h | 52.8 | 20,500 | 1.09 |
| 47 | 3i | 59.5 | 26,500 | 1.08 |
| 48 | 4a | 18.4 | 6,600 | 1.08 |
| 49 | 4b | 23.2 | 8,200 | 1.08 |

EXAMPLE 50

<Preparation of Solution for Polymerization>

In this example, a proportion of the compound (23), methyl methacrylate, cuprous bromide and L-(-)-sparteine in the solution for polymerization was set in this order to 1:500:0.5:1 in terms of a mole ratio. Anisole was used so that a concentration of methyl methacrylate in the solution for polymerization was 50 wt %.

A compound (23)/methyl methacrylate/L-(-)-sparteine/ anisole solution and cuprous bromide were separately introduced into a feed forked heat resistant glass-made ampoule in a draft which was cut off from a UV ray. Then, freezing vacuum deaeration (pressure: 1.0 Pa) was carried out by means of the vacuum device equipped with an oil-sealed rotary pump while taking care so that both were not mixed. The frozen solution was molten at a room temperature, and then dry argon gas was filled therein. The operation of carrying out freezing vacuum deaeration and filling of argon gas was repeated three times in total, and then the compound (23)/methyl methacrylate/L-(-)-sparteine/anisole solution was mixed with cuprous bromide in the feed forked heat resistant glass-made ampoule while maintaining a state of filling argon, followed by quickly sealing the ampoule by means of a hand burner.

<Polymerization and Analysis>

The sealed heat resistant glass-made ampoule was set in a constant temperature shaking bath, and polymerization was carried out to obtain a brown viscous solution of a polymer (5a). In this case, the polymerization temperature was 70° C., and the polymerization time was 2 hours. A molecular weight and a molecular weight distribution of the polymer (5a) were determined in the same manner as in Example 31, and the results thereof are shown in Table 6. Further, a heat decomposition temperature of the polymer (5a) was determined, and the result thereof is shown in Table 6.

EXAMPLE 51

Polymerization was carried out in the same manner as in Example 50 to obtain a solution of a polymer (5b), except that in this example, a proportion of the compound (23), methyl methacrylate, cuprous bromide and L-(-)-sparteine in the solution for polymerization was set in this order to 1:500:1:2 1 in terms of a mole ratio and that the polymerization time was changed to 2 hours. A molecular weight and a molecular weight distribution of the polymer (5b) were determined in the same manner as in Example 31, and the results thereof are shown in Table 6. Further, a glass transition point and a heat decomposition temperature of the polymer (5b) were determined, and the results thereof are shown in Table 6.

EXAMPLE 52

<Preparation of Solution for Polymerization>

In this example, a proportion of the compound (23), methyl methacrylate, cuprous bromide and L-(-)-sparteine in the solution for polymerization was set in this order to 1:500:2:4 in terms of a mole ratio. Anisole was used so that a concentration of methyl methacrylate in the solution for polymerization was 50 wt %.

A compound (23)/methyl methacrylate/L-(-)-sparteine/ anisole solution and cuprous bromide each were separately introduced into a feed forked heat resistant glass-made ampoule in a draft which was cut off from a UV ray. Then, freezing vacuum deaeration (pressure: 1.0 Pa) was carried out three times by means of the vacuum device equipped with an oil-sealed rotary pump while taking care so that both were not mixed. The silicon compound/methyl methacrylate/L-(-)-sparteine/anisole solution was mixed with cuprous bromide in the feed forked heat resistant glass-made ampoule while maintaining a state of vacuum, and then the ampoule was quickly sealed by means of a hand burner.

<Polymerization and Analysis>

The sealed heat resistant glass-made ampoule was set in a constant temperature shaking bath, and polymerization was carried out to obtain a brown viscous solution of a polymer (6a). In this case, the polymerization temperature was 70° C., and the polymerization time was 2 hours. The monomer conversion rate and a molecular weight and a molecular weight distribution of the polymer (6a) were determined in the same manner as in Example 31, and the results thereof are shown in Table 6. Further, a heat decomposition temperature of the polymer (6a) was determined, and the result thereof is shown in Table 6.

EXAMPLE 53

Polymerization was carried out in the same manner as in Example 52 to obtain a brown viscous solution of a polymer (6b), except that the polymerization time was changed to 3 hours. The monomer conversion rate and a molecular weight and a molecular weight distribution of the polymer (6b) were determined in the same manner as in Example 31, and the results thereof are shown Table 6. Further, a glass transition temperature and a heat decomposition temperature of the polymer (5b) were determined, and the results thereof are shown in Table 6.

EXAMPLE 54

Polymerization was carried out in the same manner as in Example 52 to obtain a brown viscous solution of a polymer (6c), except that the polymerization time was changed to 4 hours. The monomer conversion rate and a molecular weight, a molecular weight distribution, a glass transition temperature and a heat decomposition temperature of the polymer (6c) were determined in the same manner as described above, and the results thereof are shown Table 6.

EXAMPLE 55

Polymerization was carried out in the same manner as in Example 52 to obtain a brown viscous solution of a polymer (6d), except that the polymerization time was changed to 0.5 hour. The monomer conversion rate and a molecular weight, a molecular weight distribution, a glass transition temperature and a heat decomposition temperature of the polymer (6d) were determined in the same manner as described above, and the results thereof are shown Table 6.

EXAMPLE 56

Polymerization was carried out in the same manner as in Example 52 to obtain a brown viscous solution of a polymer (6e), except that the polymerization time was changed to 1.5 hour. The monomer conversion rate and a molecular weight, a molecular weight distribution, a glass transition temperature and a heat decomposition temperature of the polymer (6e) were determined in the same manner as described above, and the results thereof are shown Table 6.

EXAMPLE 57

<Preparation of Solution for Polymerization and Polymerization>

Polymerization was carried out in the same manner as in Example 57 to obtain a brown viscous solution of a polymer (6f), except that the polymerization time was changed to 2.5 hours. A molecular weight, a molecular weight distribution, a glass transition temperature and a heat decomposition temperature of the polymer (6f) were determined in the same manner as described above, and the results thereof are shown Table 6.

EXAMPLE 58

<Preparation of Solution for Polymerization and Polymerization>

Polymerization was carried out in the same manner as in Example 52 to obtain a brown viscous solution of a polymer (6 g), except that the polymerization time was changed to 2.1 hours. The monomer conversion rate and a molecular weight, a molecular weight distribution, a glass transition temperature and a heat decomposition temperature of the polymer (6 g) were determined in the same manner as described above, and the results thereof are shown Table 6.

EXAMPLE 59

Polymerization was carried out in the same manner as in Example 52 to obtain a brown viscous solution of a polymer (6h), except that the polymerization time was changed to 3.5 hours. The monomer conversion rate and a molecular weight, a molecular weight distribution, a glass transition temperature and a heat decomposition temperature of the polymer (6 h) were determined in the same manner as described above, and the results thereof are shown Table 6.

EXAMPLE 60

Polymerization was carried out in the same manner as in Example 52 to obtain a brown viscous solution of a polymer (6i), except that the polymerization time was changed to 5.5 hours. The monomer conversion rate and a molecular weight, a molecular weight distribution, a glass transition temperature and a heat decomposition temperature of the polymer (6i) were determined in the same manner as described above, and the results thereof are shown Table 6.

EXAMPLE 61

Polymerization was carried out in the same manner as in Example 52 to obtain a brown viscous solution of a polymer (6j), except that the polymerization time was changed to 7.0 hours. The monomer conversion rate and a molecular weight, a molecular weight distribution, a glass transition temperature and a heat decomposition temperature of the polymer (6j) were determined in the same manner as described above, and the results thereof are shown Table 6.

TABLE 6

| Example No. | Polymer No. | Polymerization time (hr) | Conversion rate (mol-%) | Mn | Dispersion degree (Mw/Mn) | Tg (° C.) | Td (° C.) |
|---|---|---|---|---|---|---|---|
| 50 | 5a | 2 | — | 2,700 | 1.09 | — | 394 |
| 51 | 5b | 2 | — | 3,400 | 1.09 | 111 | 379 |
| 52 | 6a | 2 | 17 | 10,300 | 1.07 | — | 375 |
| 53 | 6b | 3 | 23 | 13,400 | 1.09 | 106 | 349 |
| 54 | 6c | 4 | 34 | 21,300 | 1.11 | 111 | 353 |
| 55 | 6d | 0.5 | 7 | 3,300 | 1.11 | 107 | 392 |
| 56 | 6e | 1.5 | 10 | 5,000 | 1.10 | 109 | 389 |
| 57 | 6f | 2.5 | — | 6,700 | 1.07 | 108 | 373 |
| 58 | 6g | 2.1 | 13 | 7,600 | 1.09 | 108 | 370 |

TABLE 6-continued

| Example No. | Polymer No. | Polymerization time (hr) | Conversion rate (mol-%) | Mn | Dispersion degree (Mw/Mn) | Tg (° C.) | Td (° C.) |
|---|---|---|---|---|---|---|---|
| 59 | 6h | 3.5 | 20 | 11,800 | 1.07 | 98 | 363 |
| 60 | 6i | 5.5 | 30 | 19,400 | 1.05 | 110 | 360 |
| 61 | 6j | 7 | 52 | 33,300 | 1.10 | 112 | 342 |

Polymers can be obtained according to the examples described above by using the compounds (24) to (29) in place of the compound (23).

COMPARATIVE EXAMPLE 1

In this comparative example, a proportion of p-toluenesulfonyl chloride, methyl methacrylate, cuprous bromide and L-(−)-sparteine in the solution for polymerization was set in this order to 1:200:2:4 in terms of a mole ratio. Diphenyl ether was used so that a concentration of methyl methacrylate in the solution for polymerization was 50 wt %.

A p-toluenesulfonyl chloride/methyl methacrylate/L-(−)-sparteine/diphenyl ether solution and cuprous bromide each were separately introduced into a feed forked heat resistant glass-made ampoule in a draft which was cut off from a UV ray. Then, freezing vacuum deaeration (pressure: 1.0 Pa) was carried out three times by means of the vacuum device equipped with an oil-sealed rotary pump while taking care so that both were not mixed. The p-toluenesulfonyl chloride/methyl methacrylate/L-(−)-sparteine/diphenyl ether solution was mixed with cuprous bromide in the feed forked heat resistant glass-made ampoule while maintaining a state of vacuum, and then the ampoule was quickly sealed by means of a hand burner.

<Polymerization and Analysis>

The sealed heat resistant glass-made ampoule was set in a constant temperature shaking bath, and polymerization was carried out to obtain a brown viscous solution of a polymer (8a). In this case, the polymerization temperature was 70° C., and the polymerization time was 15 minutes. A molecular weight, a molecular weight distribution and a heat decomposition temperature of the polymer (8a) were determined in the same manner as described above, and the results thereof are shown in Table 7.

COMPARATIVE EXAMPLE 2

Polymerization was carried out in the same manner as in Comparative Example 1 to obtain a brown viscous solution of a polymer (8b), except that the polymerization time was changed to 1 hour. A molecular weight, a molecular weight distribution, a glass transition temperature and a heat decomposition temperature of the polymer (8b) were determined in the same manner as described above, and the results thereof are shown Table 7.

COMPARATIVE EXAMPLE 3

Polymerization was carried out in the same manner as in Comparative Example 1 to obtain a brown viscous solution of a polymer (8c), except that the polymerization time was changed to 2 hours. A molecular weight, a molecular weight distribution, a glass transition temperature and a heat decomposition temperature of the polymer (8c) were determined in the same manner as described above, and the results thereof are shown Table 7.

COMPARATIVE EXAMPLE 4

Polymerization was carried out in the same manner as in Comparative Example 1 to obtain a brown viscous solution of a polymer (8d), except that the polymerization time was changed to 5 hours. A molecular weight, a molecular weight distribution, a glass transition temperature and a heat decomposition temperature of the polymer (8d) were determined in the same manner as described above, and the results thereof are shown-Table 7.

COMPARATIVE EXAMPLE 5

Polymerization was carried out in the same manner as in Comparative Example 1 to obtain a brown viscous solution of a polymer (8e), except that in this comparative example, a proportion of p-toluenesulfonyl chloride, methyl methacrylate, cuprous bromide and L-(−)-sparteine in the solution for polymerization was set in this order to 1:200:1:2 in terms of a mole ratio and that the polymerization time was changed to 4 hours. A molecular weight, a molecular weight distribution, a glass transition temperature and a heat decomposition temperature of the polymer (8e) were determined in the same manner as described above, and the results thereof are shown Table 7.

COMPARATIVE EXAMPLE 6

Polymerization was carried out in the same manner as in Comparative Example 5 to obtain a brown viscous solution of a polymer (8f), except that the polymerization time was changed to 5.5 hours. A molecular weight, a molecular weight distribution, a glass transition temperature and a heat decomposition temperature of the polymer (8f) were determined in the same manner as described above, and the results thereof are shown Table 7.

COMPARATIVE EXAMPLE 7

Polymerization was carried out in the same manner as in Comparative Example 1 to obtain a solution of a polymer (8g), except that in this comparative example, a proportion of p-toluenesulfonyl chloride, methyl methacrylate, cuprous bromide and L-(−)-sparteine in the solution for polymerization was set in this order to 1:500:2:4 in terms of a mole ratio and that the polymerization time was changed to 6.3 hours. A molecular weight, a molecular weight distribution, a glass transition temperature and a heat decomposition temperature of the polymer (8g) were determined in the same manner as described above, and the results thereof are shown Table 7.

TABLE 7

| Comparative Example No. | Polymer No. | Polymerization time (hr) | Mn | Dispersion degree (Mw/Mn) | Tg (°C.) | Td (°C.) |
|---|---|---|---|---|---|---|
| 1 | 8a | 0.25 | 1,300 | 1.09 | — | 381 |
| 2 | 8b | 1 | 2,400 | 1.09 | 90 | 362 |
| 3 | 8c | 2 | 4,400 | 1.10 | 99 | 353 |
| 4 | 8d | 5 | 6,700 | 1.05 | 104 | 354 |
| 5 | 8e | 4 | 8,300 | 1.06 | 112 | 350 |
| 6 | 8f | 5.5 | 13,600 | 1.10 | 105 | 345 |
| 7 | 8g | 6.3 | 30,300 | 1.16 | 110 | 352 |

In comparison of the polymers having almost the same molecular weights, the polymers obtained by using the compound (23) as the initiator show a higher heat decomposition temperature excluding the case of the polymers having a large molecular weight.

INDUSTRIAL APPLICABILITY

The silicon compound provided by the present invention is a silsesquioxane derivative having an excellent living polymerizable radical polymerization initiating function, and it is expected to reveal characteristics which are completely different from those of conventional silsesquioxanes. For example, it is possible to commence polymerization by allowing and acryl base monomer to coexist to form an acryl base polymer making use of one point of the structure of the silsesquioxane in the present invention as a starting point. In the polymer thus obtained having an organic group of a silsesquioxane structure at an end thereof, it is possible as well to positively make use of interaction between the organic groups of the silsesquioxane structure thereof. This makes it possible to not only provide an organic-inorganic composite material having a clear structure but also control the structure of this polymer as molecular assemblies. In addition thereto, the silicon compound of the present invention has further characteristics other than a function as a polymerization initiator. For example, a halogenated sulfonyl group has a strong electrophilicity, and therefore it is possible to synthesize various silsesquioxane derivatives by reacting the silicon compound of the present invention with various nucleophilic reagents. Accordingly, the above compound can actively be used as an intermediate useful for organic synthesis.

What is claimed is:

1. A silicon compound represented by Formula (1):

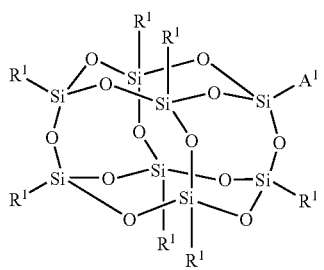

(1)

in Formula (1), seven $R^1$'s are groups independently selected respectively from the group consisting of hydrogen, alkyl, substituted or non-substituted aryl and substituted or non-substituted arylalkyl; $A^1$ is an organic group substituted with a halogenated sulfonyl group; in the alkyl group, hydrogen may be optionally replaced by fluorine, and —$CH_2$— may be optionally replaced by —O—, —CH=CH—, cycloalkylene or cycloalkenylene; and in the alkylene moiety of the arylalkyl group, hydrogen may be optionally replaced by fluorine, and —$CH_2$— may be optionally replaced by —O— or —CH=CH—.

2. The silicon compound as described in claim 1, wherein seven $R^1$'s in Formula (1) are groups independently selected respectively from the group consisting of hydrogen, alkyl having a carbon number of 1 to 45, substituted or non-substituted aryl and substituted or non-substituted arylalkyl; in the alkyl group having a carbon number of 1 to 45, hydrogen may be optionally replaced by fluorine, and —$CH_2$— may be optionally replaced by —O—, —CH=CH—, cycloalkylene or cycloalkenylene; and in the alkylene moiety of the arylalkyl group, hydrogen may be optionally replaced by fluorine, and —$CH_2$— may be optionally replaced by —O— or —CH=CH—.

3. The silicon compound as described in claim 1, wherein seven $R^1$'s in Formula (1) are groups independently selected respectively from the group consisting of hydrogen and alkyl having a carbon number of 1 to 30; and in the alkyl group having a carbon number of 1 to 30, hydrogen may be optionally replaced by fluorine, and —$CH_2$— may be optionally replaced by —O— or cycloalkylene.

4. The silicon compound as described in claim 1, wherein seven $R^1$'s in Formula (1) are groups independently selected respectively from the group consisting of alkenyl having a carbon number of 1 to 20 and a group in which —$CH_2$— is optionally replaced by cycloalkenylene in alkyl having a carbon number of 1 to 20;
in the alkenyl having a carbon number of 1 to 20, hydrogen may be optionally replaced by fluorine, and —$CH_2$— may be optionally replaced by —O— or cycloalkylene; and
in the group in which —$CH_2$— is optionally replaced by cycloalkenylene in alkyl having a carbon number of 1 to 20, hydrogen may be optionally replaced by fluorine.

5. The silicon compound as described in claim 1, wherein seven $R^1$'s in Formula (1) are groups independently selected respectively from the group consisting of naphthyl and phenyl in which hydrogen may be optionally replaced by halogen or alkyl having a carbon number of 1 to 10;
in the alkyl group having a carbon number of 1 to 10, hydrogen may be optionally replaced by fluorine, and —$CH_2$— may be optionally replaced by —O—, —CH=CH—, cycloalkylene or phenylene.

6. The silicon compound as described in claim 1, wherein seven $R^1$'s in Formula (1) are groups independently selected respectively from the group consisting of phenylalkyls in which hydrogen on a benzene ring may be optionally replaced by halogen or alkyl having a carbon number of 1 to 12;
in the alkyl group having a carbon number of 1 to 12, hydrogen may be optionally replaced by fluorine, and —$CH_2$— may be optionally replaced by —O—, —CH=CH—, cycloalkylene or phenylene; and
in the alkylene moiety of the phenylalkyl group, which has a carbon number of 1 to 12, hydrogen may be optionally replaced by fluorine, and —$CH_2$— may be optionally replaced by —O— or —CH=CH—.

7. The silicon compound as described in claim 1, wherein seven $R^1$'s in Formula (1) are groups independently selected respectively from the group consisting of alkyl having a carbon number of 1 to 8, phenyl, non-substituted naphthyl and phenylalkyl;

in the alkyl aroup having 1 to 8 carbon atoms, hydrogen may be optionally replaced by fluorine, and —CH$_2$— may be optionally replaced by —O—, —CH═CH—, cycloalkylene or cycloalkenylene;

in the phenyl, hydrogen may be optionally replaced by halogen, methyl or methoxy;

in phenyl in the phenylalkyl group, hydrogen may be optionally replaced by fluorine, alkyl having a carbon number of 1 to 4, ethenyl or methoxy; the alkylene moiety of the phenylalkyl group has a carbon number of 1 to 8, and —CH$_2$— in the alkylene moiety may be optionally replaced by —O— or —CH═CH—.

8. The silicon compound as described in claim 1, wherein seven R$^1$'s in Formula (1) are one group selected from the group consisting of alkyl having a carbon number of 1 to 8, phenyl, non-substituted naphthyl and phenylalkyl;

in the alkyl having a carbon number of 1 to 8, hydrogen may be optionally replaced by fluorine, and —CH$_2$— may be optionally replaced by —O—, —CH═CH—, cycloalkylene or cycloalkenylene;

in the phenyl, hydrogen may be optionally replaced by halogen, methyl or methoxy;

in phenyl in the phenylalkyl group, hydrogen may be optionally replaced by fluorine, alkyl having a carbon number of 1 to 4, ethenyl or methoxy;

the alkylene moiety of the phenylalkyl group has a carbon number of 1 to 8, and —CH$_2$—in the alkylene moiety may be optionally replaced by —O— or —CH═CH—.

9. The silicon compound as described in claim 1, wherein seven R$^1$'s in Formula (1) are one group selected from the group consisting of phenyl, naphthyl and phenylalkyl;

in the phenyl, hydrogen may be optionally replaced by halogen, methyl or methoxy;

in phenyl in the phenylalkyl group, hydrogen may be optionally replaced by fluorine, alkyl having a carbon number of 1 to 4, ethenyl or methoxy;

the alkylene moiety of the phenylalkyl group has a carbon number of 1 to 8, and —CH$_2$— in the alkylene moiety may be optionally replaced by —O—.

10. The silicon compound as described in claim 1, wherein seven R$^1$'s in Formula (1) are ethyl, 2-methylpropyl, 2,4,4-trimethylpentyl, 3,3,3-trifluoropropyl, cyclopentyl, cyclohexyl or non-substituted phenyl.

11. The silicon compound as described in claim 1, wherein seven R$^1$'s in Formula (1) are non-substituted phenyl.

12. The silicon compound as described in any of claims 1 to 11, wherein A$^1$ in Formula (1) described in claim 1 is a group represented by Formula (2):

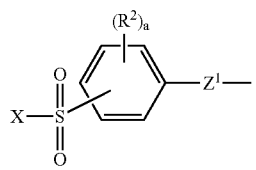

(2)

in Formula (2), X is halogen; R$^2$ is alkyl having a carbon number of 1 to 3; a is an integer of 0 to 2; Z$^1$ is a single bond or alkylene having a carbon number of 1 to 10; in the alkylene having a carbon number of 1 to 10, —CH$_2$— may be optionally replaced by —O—, —COO— or —OCO—; and both of the bonding positions of halogenated sulfonyl and R$^2$ on the benzene ring are optional positions.

13. The silicon compound as described in claim 12, wherein Z$^1$ in Formula (2) is Z$^2$—C$_2$H$_\square$—; Z$^2$ is a single bond,or alkylene having a carbon number of 1 to 8, and —CH$_2$— in the alkylene group may be optionally replaced by —O—, —COO— or —OCO—.

14. The silicon compound as described in claim 12, wherein in Formula (2), Z$^1$ is —C$_2$H$_4$—; X is chlorine or bromine; and a is 0.

15. A production process for the silicon compound represented by Formula (1) as described in claim 1, which comprises reacting a compound represented by Formula (3) with trichlorosilane having a halogenated sulfonyl group:

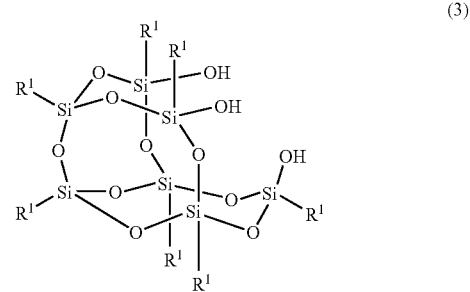

(3)

in Formula (3), seven R$^1$'s are groups independently selected respectively from the group consisting of hydrogen, alkyl, substituted or non-substituted aryl and substituted or non-substituted arylalkyl; in the alkyl group, hydrogen may be optionally replaced by fluorine, and —CH$_2$— may be optionally replaced by —O—, —CH═CH—, cycloalkylene or cycloalkenylene; and in the alkylene moiety of the arylalkyl group, hydrogen may be optionally replaced by fluorine, and —CH$_2$— may be optionally replaced by —O— or —CH═CH—.

16. A production process for a silicon compound represented by Formula (5), which comprises reacting a compound represented by Formula (3) with a compound represented by Formula (4):

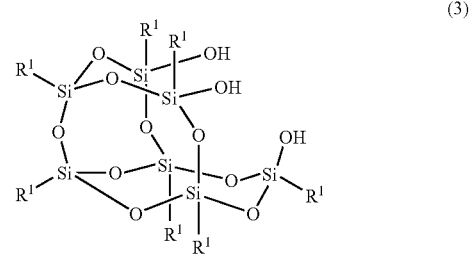

(3)

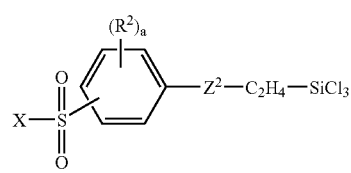

(4)

-continued (5)

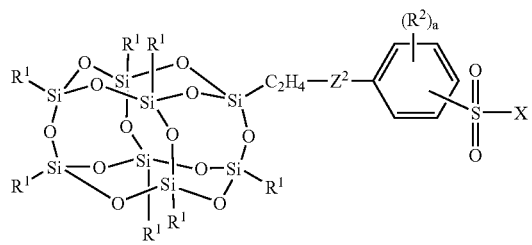

wherein $R^1$ in Formula (3) is one group selected from the group consisting of alkyl having a carbon number of 1 to 8, phenyl, non-substituted naphthyl and phenylalkyl; in the alkyl group having a carbon number of 1 to 8, hydrogen may be optionally replaced by fluorine, and —$CH_2$— may be optionally replaced by —O—, —CH═CH—, cycloalkylene or cycloalkenylene; hydrogen in the phenyl may be optionally replaced by halogen, methyl or methoxy; in the phenylalkyl, hydrogen on a benzene ring may be optionally replaced by fluorine, alkyl having a carbon number of 1 to 4, ethenyl or methoxy, and —$CH_2$— in the alkylene moiety may be optionally replaced by —O—; $R^1$ in Formula (5) has the same meaning as that of $R^1$ in Formula (3); in Formula (4), X is halogen; $R^2$ is alkyl having a carbon number of 1 to 3; a is an integer of 0 to 2; $Z^2$ is a single bond or alkylene having 1 to 8 carbon atoms; in the alkylene group having a carbon number of 1 to 8, —$CH_2$— may be optionally replaced by —O—, —COO— or —OCO—; both of the bonding positions of halogenated sulfonyl and $R^2$ on the benzene ring are optional positions; and the meanings of X, $R^2$, and $Z^2$ in Formula (5) and the bonding positions of halogenated sulfonyl and $R^2$ on the benzene ring are the same as those in Formula (4).

17. A production process for the silicon compound represented by Formula (1) as described in claim 1, which comprises reacting a compound represented by Formula (6) with trichlorosilane having a halogenated sulfonyl group:

(6)

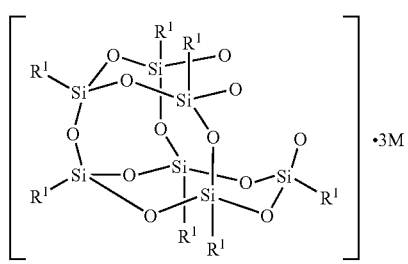

in Formula (6), seven $R^1$'s are groups independently selected respectively from the group consisting of hydrogen, alkyl, substituted or non-substituted aryl and substituted or non-substituted arylalkyl; M is a monovalent alkali metal atom; in the alkyl group, hydrogen may be optionally replaced by fluorine, and —$CH_2$—may be optionally replaced by —O—, —CH═CH—, cycloalkylene or cycloalkenylene; and in the alkylene moiety of the arylalkyl group, hydrogen may be optionally replaced by fluorine, and —$CH_2$— may be optionally replaced by —O— or —CH═CH—.

18. A production process for a silicon compound represented by Formula (5), which comprises reacting a compound represented by Formula (6) with a compound represented by Formula (4):

(6)

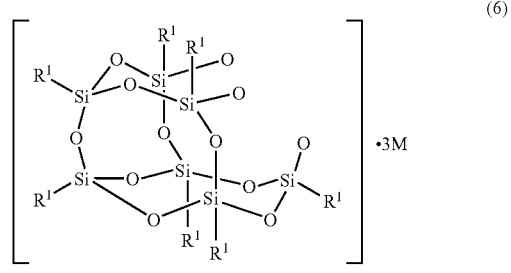

(4)

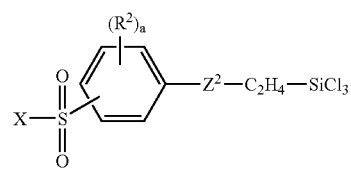

(5)

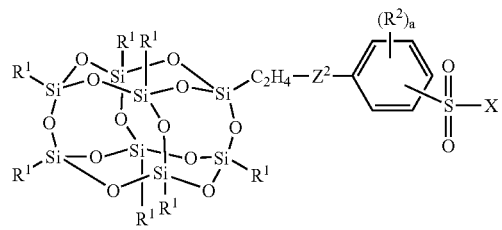

in Formula (6), $R^1$ is one group selected from the group consisting of alkyl having a carbon number of 1 to 8, phenyl, non-substituted naphthyl and phenylalkyl; M is a monovalent alkali metal atom; in the alkyl group having a carbon number of 1 to 8, hydrogen may be optionally replaced by fluorine, and —$CH_2$— may be optionally replaced by —O—, —CH═CH—, cycloalkylene or cycloalkenylene; hydrogen in the phenyl may be optionally replaced by halogen, methyl or methoxy; in the phenylalkyl group, hydrogen on a benzene ring may be optionally replaced by fluorine, alkyl having 1 to 4 carbon atoms, ethenyl or methoxy, and —$CH_2$—in the alkylene moiety may be optionally replaced by —O—;

$R^1$ in Formula (5) has the same meaning as that of $R^1$ in Formula (6); in Formula (4), X is halogen; $R^2$ is alkyl having 1 to 3 carbon atoms; a is an integer of 0 to 2; $Z^2$ is a single bond or alkylene having a carbon number of 1 to 8; in the alkylene group having a carbon number of 1 to 8, —$CH_2$— may be optionally replaced by —O—, —COO— or —OCO—; both of the bonding positions of halogenated sulfonyl and $R^2$ on the benzene ring are optional positions; and the meanings of X, $R^2$, and $Z^2$ in Formula (5) and the bonding positions of halogenated sulfonyl and $R^2$ on the benzene ring are the same as those in Formula (4).

19. A polymer obtained by polymerizing a vinyl base monomer using the silicon compound represented by Formula (1) as described in claim 1 as an initiator and a transition metal complex as a catalyst.

20. A polymer represented by Formula (7) obtained by polymerizing a vinyl base monomer using the silicon compound represented by Formula (1) as described in claim 18 as an initiator and a transition metal complex as a catalyst:

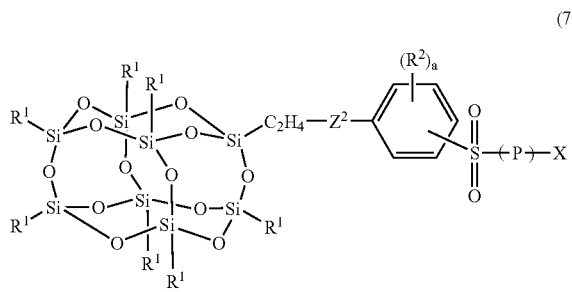

(7)

the meanings of $R^1$, $Z^2$, $R^2$, a and X in Formula (7) and the bonding positions of halogenated sulfonyl and $R^2$ on the benzene ring are the same as those in Formula (6) as described in claim 18, and P is a vinyl base polymer.

21. The polymer as described in claim 19 or 20, wherein the vinyl base monomer is at least one selected from the group consisting of a (meth)acrylic acid derivative and a styrene derivative.

22. The polymer as described in claim 19 or 20, wherein the vinyl base monomer is at least one selected from the group consisting of the (meth)acrylic acid derivatives.

23. A polymerization process for a vinyl base monomer which comprises using the silicon compound represented by Formula (1) as described in claim 1 as an initiator and using a transition metal complex as a catalyst.

24. A production process for the polymer represented by Formula (7):

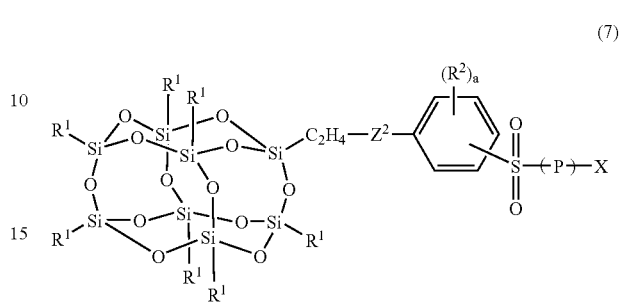

(7)

the meanings of $R^1$, $Z^2$, $R^2$, a and X in Formula (7) and the bonding positions of halogenated sulfonyl and $R^2$ on the benzene ring are the same as those in Formula (6) as described in claim 18, and P is a vinyl base polymer, which comprises polymerizing a vinyl base monomer using the compound represented by Formula (5) as described in claim 18 as an initiator and using a transition metal complex as a catalyst.

* * * * *